US012734129B2

United States Patent

(12) United States Patent
Angle et al.

(10) Patent No.: US 12,734,129 B2
(45) Date of Patent: Sep. 15, 2026

(54) LIPOSOMES ENCAPSULATING ADENOSINE

(71) Applicants: New York University, New York, NY (US); Regenosine, Inc., Jersey City, NJ (US)

(72) Inventors: Siddhesh R. Angle, Metuchen, NJ (US); Carmen Corciulo, Gothenburg (SE); Bruce N. Cronstein, Bridgewater, CT (US); Jonathan Kaufman, Pittsburgh, PA (US)

(73) Assignees: New York University, New York, NY (US); Regenosine, Inc., Jersey City, NJ (US)

( * ) Notice: Subject to any disclaimer, the term of this patent is extended or adjusted under 35 U.S.C. 154(b) by 198 days.

(21) Appl. No.: 18/465,726

(22) Filed: Sep. 12, 2023

(65) Prior Publication Data

US 2023/0414508 A1 Dec. 28, 2023

Related U.S. Application Data

(63) Continuation-in-part of application No. 18/159,675, filed on Jan. 25, 2023, which is a continuation of (Continued)

(51) Int. Cl.

| | |
|---|---|
| ***A61K 9/1274*** | (2025.01) |
| ***A61K 9/00*** | (2006.01) |
| ***A61K 31/7076*** | (2006.01) |

(52) U.S. Cl.
CPC .......... *A61K 9/1274* (2013.01); *A61K 9/0019* (2013.01); *A61K 31/7076* (2013.01)

(58) Field of Classification Search
CPC ..... A61K 9/1274; A61K 9/127; A61K 9/1271
See application file for complete search history.

(56) References Cited

U.S. PATENT DOCUMENTS

| | | | |
|---|---|---|---|
| 5,814,335 A | 9/1998 | Webb et al. | |
| 5,932,558 A | 8/1999 | Cronstein et al. | |

(Continued)

FOREIGN PATENT DOCUMENTS

| | | |
|---|---|---|
| KR | 10073710 A | 7/2007 |
| WO | 2015095576 A1 | 6/2015 |

OTHER PUBLICATIONS

Carmen Corciulo et al. "Endogenous adenosine maintains cartilage homeostasis and exogenous adenosine inhibits osteoarthritis progression." Nature Communications, vol. 8:15019, 2017, pp. 1-13 and 20 pages of supplemental information. (Year: 2017).*

(Continued)

*Primary Examiner* — Isaac Shomer
(74) *Attorney, Agent, or Firm* — Hodgson Russ LLP

(57) ABSTRACT

Provided are liposomes that encapsulate adenosine. The liposomes may be formed from sphingomyelin or a combination of sphingomyelin and 1,2-dimyristoyl-sn-glycero-3-phosphocholine (DMPC) or a combination of sphingomyelin and 1,2-dimyristoyl-sn-glycero-3-phosphorylglycerol (DMPG) or a combination of sphingomyelin, DMPG, and DMPC. The liposomes encapsulating adenosine may be used to induce cartilage regeneration, treat osteoarthritis, alleviate joint pain, and/or slow, arrest, and/or reverse progressive structural tissue damage associated with osteoarthritis or treat osteoarthritis, rheumatoid arthritis, acute gouty arthritis, and/or synovitis. The liposomes may release adenosine for up to two weeks.

14 Claims, 29 Drawing Sheets

Statistics : One-way (Brown-Forsythe and Welch) ANOVA. *P<0.05, P<0.01, *P<0.001 v/s vehicle, †P<0.05 v/s RgnA01

Related U.S. Application Data application No. 17/601,032, filed as application No. PCT/US2020/026658 on Apr. 3, 2020, now Pat. No. 11,607,386.

(60) Provisional application No. 63/375,345, filed on Sep. 12, 2022, provisional application No. 62/828,916, filed on Apr. 3, 2019.

(56) References Cited

U.S. PATENT DOCUMENTS

| | | | | |
|---|---|---|---|---|
| 6,015,576 | A | 1/2000 | See et al. | |
| 8,110,217 | B2 | 2/2012 | Chancellor et al. | |
| 10,441,541 | B2 | 10/2019 | Cronstein et al. | |
| 10,639,278 | B2 | 5/2020 | Kaufman et al. | |
| 11,607,386 | B2 * | 3/2023 | Angle | A61K 9/1274 |
| 2003/0235611 | A1 | 12/2003 | Ehringer et al. | |
| 2004/0062797 | A1 | 4/2004 | Loeb | |
| 2004/0082521 | A1 | 4/2004 | Singh | |
| 2006/0008909 | A1 | 1/2006 | Cullis et al. | |
| 2006/0100168 | A1 * | 5/2006 | Ravid | A61K 31/56 514/182 |
| 2007/0031480 | A1 | 2/2007 | Mayer et al. | |
| 2010/0098749 | A1 * | 4/2010 | Barenholz | A61K 9/0019 424/450 |
| 2010/0098753 | A1 * | 4/2010 | Minamino | A61P 9/10 424/450 |
| 2011/0250266 | A1 * | 10/2011 | Barenholz | A61P 29/00 424/450 |
| 2015/0343063 | A1 | 12/2015 | Helson et al. | |
| 2016/0263031 | A1 | 9/2016 | Kaufmann et al. | |
| 2018/0036238 | A1 | 2/2018 | Cronstein et al. | |

OTHER PUBLICATIONS

Corciulo, C., et al, "Endogenous adenosine maintains cartilage homeostasis and exogenous adenosine inhibits osteoarthritis progression," Nature Communications, May 11, 2017, vol. 8, Issue 15019.

Strazzula, L.C., et al, "Regulation of bone and cartilage by adenosine signaling," Purinergic Signalling, Jul. 29, 2016, pp. 583-593, vol. 12.

Bar, L.K., et al, "Effect of Sphingomyelin Composition on the Phase Structure of Phosphatidylcholine-Sphingomyelin Bilayers," Biochemistry, Mar. 4, 1997, pp. 2507-2516, vol. 36, Issue 9.

Egerdie, R.B., et al., "The Effect of Liposome Encapsulated Antineoplastic Agents on Transitional Cell Carcinoma in Tissue Culture," The Journal of Urology, Part 1, Aug. 1, 1989, pp. 390-398, vol. 142, No. 2.

Shah, J., et al., "Structural and thermotropic properties of synthetic C16:0 (palmitoyl) ceramide: effect of hydration," Journal of Lipid Research, Sep. 1, 1995, pp. 1936-1944, vol. 36, No. 9.

Yatvin, M.B., et al., "Design of Liposomes for Enhanced Local Release of Drugs by Hyperthermia," Science, Dec. 22, 1978, pp. 1290-1293, vol. 202, No. 4374.

Hsueh, Y-W., et al., "The Effect of Ceramide on Phosphatidylcholine Membranes: A Deuterium NMR Study," Biophysical Journal, Jan. 6, 2009, pp. 3089-3095, vol. 82, No. 6.

Allen et al., Large unilamellar liposomes with low uptake into the reticuloendothelial system, FEBS Letters, Oct. 1987, vol. 223, No. 1, pp. 42-46.

Vissers Caroline et al, "Nanoparticle technology and stem cell therapy team up against neurodegenerative disorders," Advanced Drug Delivery Reviews, Dec. 3, 2019, vol. 148, pp. 239-251.

Bekisz Jonathan M et al, "The Role of Adenosine Receptor Activation in Attenuating Cartilaginous Inflammation," Inflammation, Apr. 14, 2018, vol. 41, No. 4, pp. 1135-1141.

* cited by examiner

Statistics : One-way (Brown-Forsythe and Welch) ANOVA. *P<0.05 v/s vehicle, †P<0.05 v/s 0.3mg

| Study Months | 0 | 1 | 2 | 3 | 4 | 5 | 6 | 7 | 8 |
|---|---|---|---|---|---|---|---|---|---|
| Tx Months | Pre-MR | | 0<br>Pre-Tx | 1 | 2 | 3 | 4 | 5 | 6 |
| Intervention | Surgery | | OA evident<br>1st injection | 2nd injection | 3rd injection | | | | Sacrifice |
| Assessments | Pain, $F^n$, cROM, Eff | | Pain, $F^n$, cROM, Eff | | | | Pain, $F^n$, cROM, Eff | | Pain, $F^n$, cROM, Eff |
| Clinical | Blood<br>Synovial Fl. | | Blood<br>Synovial Fl. | | | | Blood<br>Synovial Fl. | | Blood<br>Synovial Fl. |
| Imaging | X-ray<br>MRI | | X-ray<br>MRI | | | | X-ray | | X-ray<br>MRI |
| Pathology | | | | | | | | | Gross Eval<br>Histology |

Figure 25

LIPOSOMES ENCAPSULATING ADENOSINE

CROSS REFERENCE TO RELATED APPLICATIONS

This application claims benefit of U.S. Provisional Application No. 63/375,345, filed on Sep. 12, 2022. This application is also is a continuation-in-part of U.S. application Ser. No. 18/159,675, filed on Jan. 25, 2023, which is a continuation of U.S. patent application Ser. No. 17/601,032, filed on Oct. 1, 2021, now U.S. Pat. No. 11,607,386, which is a national stage application of International Application No. PCT/US2020/026658, filed on Apr. 3, 2020, which claims benefit of U.S. Provisional Application No. 62/828,916, filed on Apr. 3, 2019.

STATEMENT REGARDING FEDERALLY SPONSORED RESEARCH

This invention was made with government support under contract no. R44AR078691 awarded by the National Institutes of Health. The government has certain rights in the invention.

BACKGROUND OF THE DISCLOSURE

Osteoarthritis (OA), a disease characterized by cartilage loss and the most common type of arthritis, affects 151 million people worldwide, including nearly 10% of the population of the United States and other industrialized countries. Age, prior trauma, obesity, and genetics are among the risk factors for developing this degenerative joint disorder. The incidence of OA increases with age, and the resulting pain, loss of joint function and mobility, social isolation, and broadly reduced quality of life make OA a condition with a high medical and social impact. OA can affect any joint, but most commonly affects the knee, hip, and hand. The prevalence of OA is greatest in the knee joint, in both women (47%) and men (40%). Current treatment options are less than optimal and do not correct the underlying problem. Therapy is mostly palliative, including use of nonsteroidal anti-inflammatory drugs (e.g. ibuprofen), narcotic analgesics, exercise, and acupuncture. The FDA has also approved OA-specific treatments, including corticosteroids (anti-inflammatory agents) and hyaluronic acid (lubrication, pain relief), all of which are delivered via intraarticular (IA) injection. While these injectable agents provide symptomatic relief, none are restorative.

The purinergic system plays a critical role in maintaining cartilage homeostasis. Adenosine, acting at its A2A receptor (A2AR), is a critical autocrine homeostatic factor that maintains chondrocyte and cartilage balance. Adenosine is an endogenously produced physiological regulator, and its intracellular and extracellular concentrations are tightly controlled by oxygen consumption, cellular stress, and mitochondrial functionality. Extracellular adenosine derives mainly from hydrolysis of ATP (primarily, but not exclusively, by the ectoenzymes CD39 and CD73) and mediates its effects via activation of G-protein-coupled receptors (A1R, A2AR, A2BR, and A3R). These adenosine receptors are highly conserved evolutionarily, and their expression and function tend to be conserved as well. Adenosine has long been known to regulate inflammation and immune responses, and previous work has demonstrated the importance of adenosine and its receptors in osteoblast, osteoclast, and bone marrow homeostasis. Prior studies have suggested that adenosine receptors also regulate chondrocyte physiology and pathology in response to inflammatory stimuli in rodent, equine, bovine, and human chondrocytes, although the specific receptor(s) involved have not been identified. Removal of endogenous adenosine (by addition of adenosine deaminase) or blockade of A2AR leads to cartilage degradation in equine cartilage explants, although equine purine metabolism differs from that of other species, as adenosine deaminase, present in the lymphocytes, plasma, and extracellular fluid of most species, is not present in horse lymphocytes or serum. A3R stimulation has been reported to diminish OA development in a chemically induced model of OA, principally due to the anti-inflammatory effects of A3R agonists. However, adenosine has a half-life of mere seconds.

BRIEF SUMMARY OF DISCLOSURE

The present disclosure provides injectable formulations. Also disclosed are methods of making and using the injectable formulations. The injectable formulations comprise liposomes and saline, where the liposomes encapsulate adenosine.

BRIEF DESCRIPTION OF THE FIGURES

For a fuller understanding of the nature and objects of the disclosure, reference should be made to the following detailed description taken in conjunction with the accompanying figures.

FIG. 25 shows the experimental process used to evaluate efficacy of liposomal formulation of adenosine for pain relief and maintenance of function and cartilage structure in dogs.

DETAILED DESCRIPTION OF THE DISCLOSURE

Figure 1:
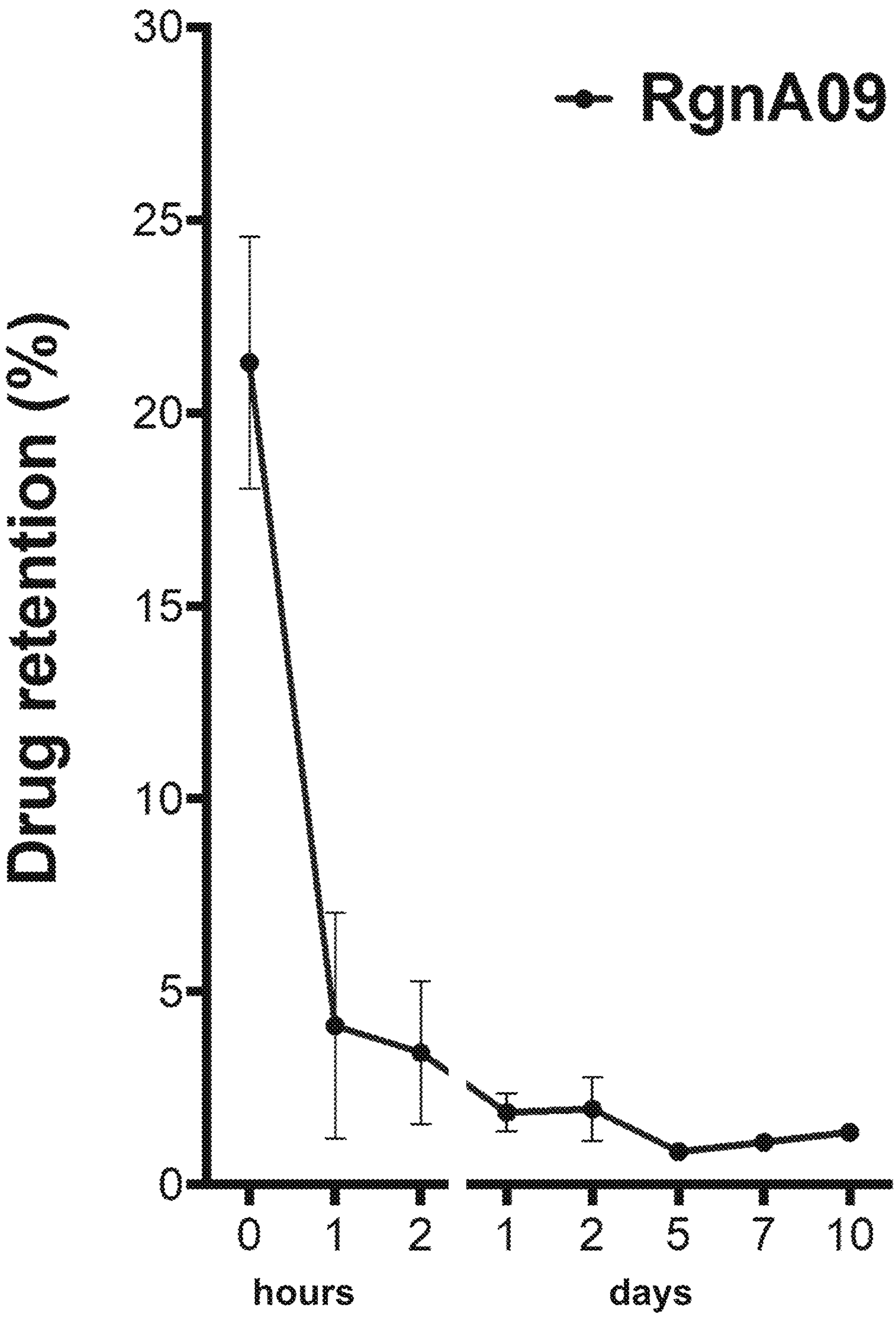
FIG. 1 shows adenosine retention of liposomes formed from RgnA09.
Figure 2:
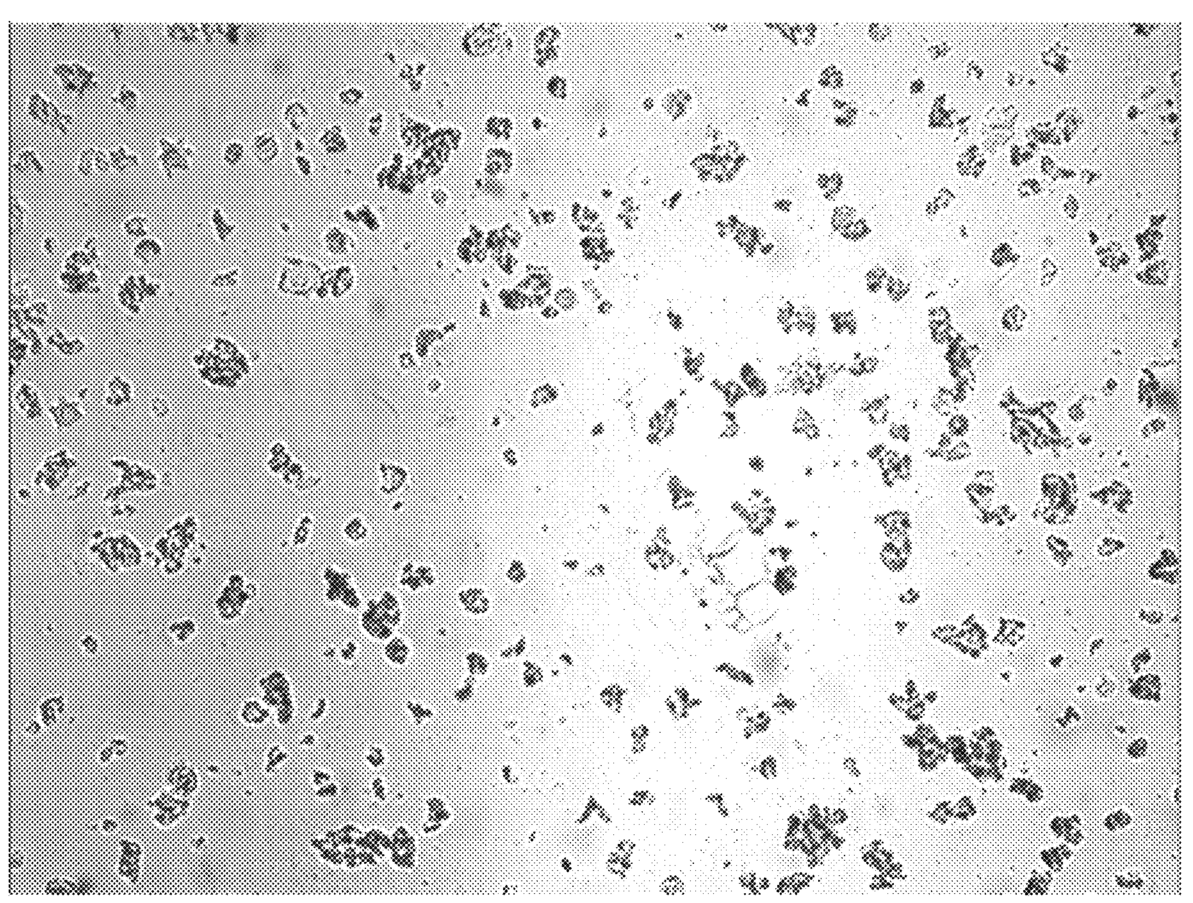
FIG. 2 shows a microscopy image of a liposomal suspension formed from RgnA09.
Figure 3:
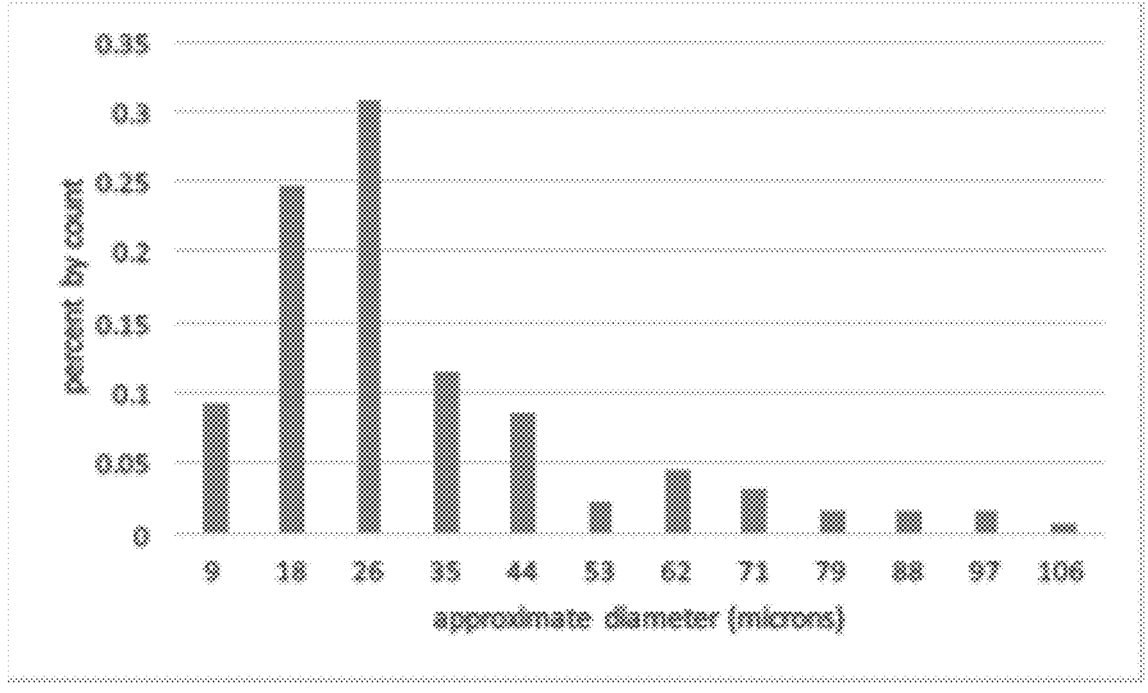
FIG. 3 shows a histogram of the approximate diameter of liposomes formed from RgnA09.

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

As used herein, unless otherwise indicated, "about", "substantially", or "the like", when used in connection with a measurable variable (such as, for example, a parameter, an amount, a temporal duration, or the like) or a list of alternatives, is meant to encompass variations of and from the specified value including, but not limited to, those within experimental error (which can be determined by, e.g., a given data set, an art accepted standard, etc. and/or with, e.g., a given confidence interval (e.g., 90%, 95%, or more confidence interval from the mean), such as, for example, variations of +/−10% or less, +/−5% or less, +/−1% or less, and +/−0.1% or less of and from the specified value), insofar such variations in a variable and/or variations in the alternatives are appropriate to perform in the instant disclosure. As used herein, the term "about" may mean that the amount or value in question is the exact value or a value that provides equivalent results or effects as recited in the claims or taught herein. That is, it is understood that amounts, sizes, compositions, parameters, and other quantities and characteristics are not and need not be exact, but may be approximate and/or larger or smaller, as desired, reflecting tolerances, conversion factors, rounding off, measurement error, or the like, or other factors known to those of skill in the art such that equivalent results or effects are obtained. In general, an amount, size, composition, parameter, or other quantity or characteristic, or alternative is "about" or "the like," whether or not expressly stated to be such. It is understood that where "about," is used before a quantitative value, the parameter also includes the specific quantitative value itself, unless specifically stated otherwise.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "0.1% to 5%" should be interpreted to include not only the explicitly recited values of 0.1% to 5%, but also, unless otherwise stated, include individual values (e.g., 1%, 2%, 3%, and 4%) and the sub-ranges (e.g., 0.5% to 1.1%, 0.5% to 2.4%, 0.5% to 3.2%, and 0.5% to 4.4%, and other possible sub-ranges) within the indicated range. It is also understood (as presented above) that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about", it will be understood that the particular value forms a further disclosure. For example, if the value "about 10" is disclosed, then "10" is also disclosed.

As used herein, the terms "including," "containing," and "comprising" are used in their open, non-limiting sense.

As used in this disclosure, the singular forms include the plural forms and vice versa unless the context clearly indicates otherwise.

The articles "a" and "an" are used in this disclosure to refer to one or more than one (i.e., to at least one) of the grammatical object of the article. By way of example, "an element" means one element or more than one element.

As used herein, unless otherwise stated or indicated, "s" refers to second(s), "min" refers to minute(s), and "h" refers to hour(s).

The phrase "therapeutically effective amount" is used herein to mean an amount sufficient to reduce by at least about 15 percent, preferably by at least 50 percent, more preferably by at least 90 percent, and most preferably prevents oxidative stress in the individual. Alternatively, a therapeutically effective amount is sufficient to cause an improvement in a clinically significant condition in the individual.

The present disclosure provides injectable formulations. Also disclosed are methods of making and using the injectable formulations.

In an aspect, the present disclosure provides injectable formulations comprising liposomes and saline, where the liposomes encapsulate adenosine.

Liposomes may comprise i) sphingomyelin or ii) sphingomyelin and 1,2-dimyristoyl-sn-glycero-3-phosphocholine (DMPC) or iii) a combination of sphingomyelin and 1,2-dimyristoyl-sn-glycero-3-phosphorylglycerol (DMPG) or iv) a combination of sphingomyelin, DMPG, and DMPC. In various examples, the liposomes comprise 70 to 100% by mass sphingomyelin. Liposomes comprising less than 100% by mass sphingomyelin may further comprise up to 30% by mass (e.g., the remainder) DMPC or DMPG or a combination of DMPC and DMPG together. In an embodiment, liposomes may comprise 70 to 99.9% by mass sphingomyelin and 0.1 to 30% by mass (e.g., the remainder) DMPC or 1,2-dimyristoyl-sn-glycero-3-phosphorylglycerol (DMPG) or a combination of DMPC and DMPG together. In an embodiment, liposomes comprise 75 to 100% by mass sphingomyelin. Liposomes comprising less than 100% by mass sphingomyelin may further comprise up to 25% by mass (e.g., the remainder) DMPC or DMPG or DMPC and DMPG together. In an embodiment, liposomes comprise 75 to 99.9% by mass sphingomyelin and from 0.1 to 25% by mass (e.g., the remainder) DMPC or DMPG or DMPC and DMPG together. For example, liposomes may comprise 75, 80, 85, 90, 95, 96, 97, 98, 99, and 99.9% sphingomyelin and the remainder is DMPC, DMPG, or a combination thereof. The percent by mass refers to the total mass of phospholipids.

Liposomes may have a diameter and/or mean diameter of 50 nm to 150 μm, including all 0.1 nm values and ranges therebetween (e.g., 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm). For example, liposomes may have a diameter and/or mean diameter of 50 nm, 75 nm, 100 nm, 250 nm, 500 nm, 1 μm, 10 μm, 25 μm, 30 μm, 40 μm, 50 μm, 75 μm, or 100 μm. In an embodiment, at least 60, at least 70, at least 80, at least 90, at least 95, at least 96, at least 97, at least 98, at least 99, at least 99.9, or 100% of the liposomes have a diameter in the range of 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm. In an embodiment, there are no liposomes having a diameter greater than 150 μm. In an embodiment, less than 1% of the liposomes have a diameter greater than 150 μm. In various embodiments, a liposome may be produced by the ethanol injection method and the resulting liposomes may be smaller than liposomes formed by other methods.

In various embodiments, the liposomes have a diameter of 250 nm or less. For example, the diameter of the liposomes have a diameter 50 nm to 250 nm, 150 nm to 250 nm, 100 nm to 200 nm, 125 to 225 nm, 100 nm to 250 nm, 100 nm to 225 nm, 180 nm to 220 nm, or about 200 nm. For example, the diameter 200 nm±10% or 200 nm±5%. In various embodiments, the liposomes are prepared via extrusion. Without intending to be bound by any particular theory, it is considered that the liposomes prepared by extrusion will have a narrow size distribution. For example, the liposomes have a desirable PDI. For example, the PDI is 0.05 to 0.3, including all 0.001 values and ranges therebetween (e.g., 0.05 to 0.25, 0.05 to 0.2, 0.05 to 0.175, 0.075 to 0.3, 0.075 to 0.25, 0.075 to 0.2, 0.075 to 0.175, 0.1 to 0.3, 0.1 to 0.25, 0.1 to 0.2, 0.1 to 0.175, 0.125 to 0.175) (e.g., about 0.126, about 0.172, 0.126, or 0.172).

In various embodiments, when the liposomes are not extruded, the liposomes of the present disclosure may be a combination of unilamellar liposomes or small unilamellar vesicles (SUV) and multilamellar liposomes or multilamellar vesicles (MLV). SUVs and MLVs provide enhanced delivery due to greater stability at the site of delivery. In an embodiment, such SUVs and MLVs may be metastable. Metastable liposomes a) have a relative diameter different than 1 (e.g., the metastable liposome does not have a perfectly circular or spherical shape); b) are large enough such that the expansive stress associated with membrane bending is not strong enough to overcome the liposome's tendency toward conformational equilibrium; and c) have a longest linear dimension (e.g., diameter) of 100 nm to 150 μm, including every 0.1 nm value and range therebetween. Such liposomes collapse (e.g., constrict or contract) into a smaller stable form when subjected to a temperature (e.g., in contact with a reservoir having a temperature) of 35-45° C., including all 0.1° C. value and range therebetween (e.g., 35, 36, 37, 38, 39, 40, 41, 42, 43, 44, or 45° C.) (e.g., about (or slightly higher than) 40° C.). In an embodiment, smaller stable liposomes have a longest linear dimension (e.g., diameter) of 50 nm to 110 μm, including every 0.1 nm value and range therebetween. Additionally, the ratio of the volume enclosed by the liposomes at 25° C. relative to the volume enclosed by the liposomes following heating to a temperature that surpasses the gel-fluid phase transition of one or more lipids forming the liposomes is greater than 10. Metastable liposomes that contain a hydrophilic agent may collapse at 35-45° C., including all 0.1° C. value and range therebetween (e.g., 35, 36, 37, 38, 39, 40, 41, 42, 43, 44, or 45° C.) (e.g., approximately 40° C.) to release (e.g., gradually release) their payload (e.g., adenosine) upon such collapse (e.g., contraction or constriction). Metastable liposomes are described in U.S. Pat. Pub. No. 2016/0263031 (relevant portions of which are hereby incorporated by reference). Metastable liposomes may be referred to simply as liposomes.

The liposomes may be formulated with one or more excipients. The formulations can be in the form of a liquid or gel, preferably a liquid, for injectable application.

Liposomes are formed from one or more lipids, which can be neutral, anionic, or cationic at physiologic pH. Examples of types of lipids include, but are not limited to, sterols and lipids such as cholesterol, phospholipids, lysolipids, lysophospholipids, sphingolipids or PEGylated lipids. In an embodiment, the carbon chain length of the phospholipids is $C_{10}$ to $C_{22}$ length. In an embodiment, the carbon chain length of the phospholipids is $C_{14}$ to $C_{20}$. Suitable lipids include, but are not limited to, phosphatidylcholine (PC) (such as egg PC, soy PC) and phosphatidylglycerols. Examples of PCs include, such as, for example, 1,2-dioleoylphosphatidylcholine (DOPC), 1,2-distearoyl phosphatidylcholine (DSPC), 1,2-dipalmitoyl phosphatidylcholine (DPPC), and 1,2-dimyristoyl phosphatidylcholine (DMPC). Various phosphatidylglycerols may be used. Non-limiting examples of phosphatidylglycerols include 1,2-dioleoyl phosphatidylglycerol (DOPG), 1,2-distearoyl phosphatidylglycerol (DSPG), 1,2- dipalmitoyl phosphatidylglycerol (DPPG), and 1,2-dimyristoyl-sn-glycero-3-phosphorylglycerol (DMPG).

In an embodiment, the phospholipids are sphingomyelin, or sphingomyelin with DMPC or DMPG, or a combination thereof. The total lipid concentration may be 7 to 200 mg/mL, including all 0.01 mg/mL values and ranges therebetween. In an embodiment, the total lipid concentration is 10, 20, 50, 75, 100, 150 or 200 mg/mL. In an embodiment where the liposome comprises sphingomyelin, DMPC, and DMPG, the ratio of DMPC to DMPG is 6 to 4 to 8 to 2. In an embodiment, the ratio of DMPC to DMPG is 7 to 3.

The liposomes have an aqueous compartment. The aqueous compartment can contain water and adenosine. The concentration of adenosine may be 0.1 to 7 mg/mL, including all 0.01 mg/mL values and ranges therebetween. In an embodiment, the concentration of adenosine may be 0.1 to 4 mg/mL. In an embodiment, the concentration of adenosine is 3 mg/mL.

The liposomes of the present disclosure may have a desirable encapsulation efficiency (EE %). Without intending to be bound by any particular theory, it is considered that the concentration of lipid increases the EE %. For example, when the lipid concentration of the liposomes is 20 mg/mL, the EE % is 2.5% or greater. For example, when the lipid concentration of the liposomes is 50 mg/mL, the EE % is 6% or greater. For example, when the lipid concentration of the liposomes is 75 mg/mL, the EE % may be 10% or greater. For example, when the lipid concentration of the liposomes is 100 mg/mL, the EE % may be 15% or greater.

Various methods of manufacturing liposomes are described herein. In an embodiment, dehydrated liposomes are prepared from a homogenous dispersion of a phospholipid, preferably sphingomyelin, in a water/tert-butyl alcohol (TBA) co-solvent system at a ratio of 2:1 mg phospholipid to mL water/TBA. Various ratios of water to TBA may be used (e.g., 10:1, 9:1, 8:1: 7:1, 6:1, 5:1. 4:1, 3:1, 2:1, 9:2, 7:2, 5:2, 3:2, 10:3, 8:3, 7:3, 5:3 (water: TBA)). The isotropic monophasic solution of liposomes is freeze dried to generate dehydrated liposomal powder in a sterile vial. The freeze drying step leaves empty lipid vesicles or dehydrated liposomes after removing both water and TBA from the vial. On addition of a pharmaceutically acceptable carrier, such as water, physiological saline or PBS, the lyophilized product spontaneously forms a large, metastable liposome dispersion. The ratio of lipid to TBA is an important factor affecting the size and the polydispersity of resulting liposome preparation.

In an embodiment, dehydrated metastable liposomes, such as, for example, RgnA09, are prepared from a solution comprising a dispersion of a plurality of phospholipids in a TBA/water co-solvent system having a 1:1 ratio by volume of water to TBA. For example, for a solution comprising 100 mg of phospholipids, 1-50 mL (e.g., 1, 2, 3, 4, 5, 6, 7, 8, 9, 10, 20, 25, 30, 40, or 50 mL) of a 1:1 ratio by volume of TBA: water co-solvent system is used. The plurality of phospholipids may be a mixture of 75% sphingomyelin (by mass) and a 25% PC/PG mixture (by mass), where the PC/PG mixture comprises 70% (by mass) DMPC and 30% (by mass) DMPG (e.g., of the total plurality of phospholipids comprising sphingomyelin and the PC/PG mixture, 70% (by mass) of the plurality of phospholipids is sphingomyelin, 17.5% (by mass) of the plurality of phospholipids is DMPC, and 7.5% (by mass) is DMPG). The resulting solution comprising the plurality of phospholipids is freeze dried to generate a dehydrated liposomal powder in a sterile vile. The lyophilate (e.g., the dehydrated liposomal powder) may then be rehydrated with a solution comprising adenosine (e.g., for 100 mg phospholipids, 10 mL of an aqueous solution comprising adenosine (e.g., a saline solution comprising adenosine, where the adenosine has a concentration of 0.1 to 7 mg/mL (e.g., 3 mg/mL)) is used to rehydrate the lyophilate).

In an embodiment, dehydrated metastable liposomes, such as, for example, RgnA10, are prepared from a solution comprising a dispersion of phospholipid in a TBA/water co-solvent system having a 3:2 ratio by volume of water to TBA. For example, for a solution comprising 100 mg of phospholipids, 1-50 mL (e.g., 1, 2, 3, 4, 5, 6, 7, 8, 9, 10, 20, 25, 30, 40, or 50 mL) of a 3:2 ratio by volume of water: TBA co-solvent system is used. The phospholipid may be sphingomyelin. The resulting solution comprising the phospholipid is freeze dried to generate a dehydrated liposomal powder in a sterile vial. The lyophilate (e.g., the dehydrated liposomal powder) may then be rehydrated with a solution comprising adenosine (e.g., for 100 mg phospholipids, 10 mL of an aqueous solution comprising adenosine (e.g., a saline solution comprising adenosine, where the adenosine has a concentration of 0.1 to 7 mg/mL (e.g., 3 mg/mL)) is used to rehydrate the lyophilate).

Various methods may be used to manufacture liposomes of the present disclosure. For example, methods to manufacture include, but are not limited to, the emulsion method, the reverse-phase evaporation method, the detergent depletion method, and the ethanol injection method. Various other methods are known in the art and are encompassed within the scope of this disclosure.

In various other examples, the liposomes are prepared via a step-down extrusion method. Using syringes, the MLV solution was extruded with multiple passes with 400 nm extruder at 65° C. with a total extrusion rate of 3 mL/min. The resulting solution was then extruded with multiple passes with 200 nm extruder at 65° C. with a total extrusion rate of 3 mL/min. The extrusion may be followed by one or more (e.g., 4) freeze and thaw cycles. In various examples, For studies on Ade EE % as a function of nanoscale extrusion pore size, the following Ade-encapsulated sample groups were extruded according to the following step-down procedures: (i) 1000 nm: multiple passes with 1000 nm extruder; (ii) 400 nm: multiple passes with 400 nm extruder; (iii) 200 nm: sequential extrusion comprising multiple passes with 400 nm extruder and multiple passes with 200 nm extruder; (iv) 100 nm: sequential extrusion comprising multiple passes with 400 nm extruder, multiple passes with 200 nm extruder, and multiple passes with 100 nm extruder.

Liposomal-adenosine suspensions may be prepared by methods of the present disclosure. The dehydrated liposomal powder is hydrated via addition of an adenosine solution and then mixed. For example, 10 mL of an adenosine solution (e.g., 3 mg/ml adenosine solution in saline (e.g., 0.9% by mass sodium chloride (9 mg of NaCl per mL of water)) is added to a vial containing 100 mg of the dehydrated liposomal powder. The resulting liposomes comprising adenosine may be multilamellar. The liposomes comprising adenosine may have a longest linear dimension (e.g., diameter) of 50 nm to 150 μm, including all 0.1 nm values and ranges therebetween (e.g., 50 nm to 1 μm, 50 nm to 750 μm, 50 to 500 nm, 50 to 250 nm, 50 to 100 nm, 100 nm to 1 μm, 100 to 750 nm, 100 to 500 nm, 100 to 250 nm, 1 to 150 μm, 1 to 100 μm, 1 to 50 μm, 1 to 40 μm, 1 to 30 μm, 1 to 25 μm, 1 to 20 μm, 1 to 10 μm, 1 to 5 μm).

In various examples, the liposomes prepared via extrusion are single vesicle or unilamellar liposomes. The unilamellar liposomes have a narrow size distribution to which they are extruded. Without intending to be bound by any particular theory, it is considered that the diameter of liposome increases the EE %. For example, when the lipid concentration of the liposomes is 50 mg/mL, and the diameter is around 100 nm the EE % is 4% or greater. For example, when the lipid concentration of the liposomes is 50 mg/mL, and the diameter is around 200 nm the EE % is 8% or greater. For example, when the lipid concentration of the liposomes is 50 mg/mL, and the diameter is around 400 nm the EE % is 15% or greater. For example, when the lipid concentration of the liposomes is 100 mg/mL, and the diameter is around 100 nm the EE % is 8% or greater. For example, when the lipid concentration of the liposomes is 100 mg/mL, and the diameter is around 200 nm the EE % is 10% or greater. For example, when the lipid concentration of the liposomes is 100 mg/mL, and the diameter is around 400 nm the EE % is 17% or greater.

The selected dosage depends upon the desired therapeutic effect, on the route of administration, and on the duration of the treatment desired. Generally dosage levels of 0.001 to 10 mg/kg of body weight daily are administered to mammals (e.g., individuals). Generally, for intravenous injection or infusion, dosage may be lower.

Compositions may also be administered orally, by parenteral (intramuscular, intraperitoneal, intravenous (IV) or subcutaneous injection), transdermal (either passively or using iontophoresis or electroporation), intraarticular (administered by entering a joint) or transmucosal (nasal, vaginal, rectal, or sublingual) routes of administration and can be formulated in dosage forms appropriate for each route of administration. In an embodiment, the formulation is injected directly into the joint of an individual. In various embodiments, a formulation or composition of the present disclosure may be injected directly into any synovial joint in an individual in need of treatment. Non-limiting examples of synovial joints include limb joints, such as, for example, shoulders, hips, knees, elbows, ankle, interphalangeal joints, or any other joint found between one or more bones that move against each other. Examples of individuals are disclosed herein.

Metastable liposomes containing adenosine of the present disclosure have several advantages. For example, the metastable liposomes have slow release of the adenosine, thus extending the biological activity of the delivered adenosine and/or reduce the dosage required.

Different size dosage units of the metastable liposomal formulation may be used. A dosage unit containing a dry powder of dehydrated metastable pre-liposomal lyophilate or an aqueous solution of adenosine or other hydrophilic active agent can be reconstituted in a container with a pharmaceutically acceptable carrier. Preferably, the pharmaceutically acceptable carrier is an aqueous carrier. Suitable amounts of dosage units include, but are not limited to, 0.1-1 mg, 1-3 mg, 3-10 mg, 10-20 mg and 20-50 mg. Suitable concentrations of dosage units include, but are not limited to, 0.05 mg/mL to 10 mg/mL, preferably 0.05 mg/mL to 5 mg/mL, more preferably 0.05 mg/mL to 3.5 mg/mL.

The injectable formulations of the present disclosure may be used to induce cartilage regeneration, treat osteoarthritis, alleviate joint pain, and/or slow, arrest, and/or reverse progressive structural tissue damage associated with osteoarthritis in an individual in need of treatment. In an example, the individual may have or be suspected of having osteoarthritis, rheumatoid arthritis, acute gouty arthritis, and/or synovitis. A method to induce cartilage regeneration, treat osteoarthritis, alleviate joint pain, and/or slow, arrest, and/or reverse progressive structural tissue damage associated with osteoarthritis in an individual in need of treatment comprises administering to the individual in need of treatment an injectable formulation of the present disclosure.

In various embodiments, an individual is a human or non-human mammal. Examples of non-human mammals include, but are not limited to, agricultural animals (e.g., farm animals), such as cows, hogs, sheep, and the like, as well as pet, service, or sport animals such as horses, dogs, cats, and the like. Additional non-limiting examples of individuals include rabbits, rats, and mice.

Upon administration to an individual in need of treatment, adenosine is released from the liposomes for up to two weeks. In an embodiment, following administration of the injectable formulation, adenosine is released from the liposomes within 1 second to 1 hour (e.g., 1 minute to 1 hour) of administration to the individual. In an embodiment, at least a portion of the adenosine (e.g., 1 to 20% of the adenosine) is released from the liposomes within 1 minute to 1 hour of administration to the individual. In an embodiment, at least a portion of the adenosine (e.g., 1 to 20% of the adenosine) is released within 1 second, 5 seconds, 10 seconds, 20 seconds, 30 seconds, 40 seconds, 50 seconds, 1 minute, 2 minutes, 3 minutes, 4 minutes, 5 minutes, or 10 minutes of administration the individual.

The injectable formulation may be administered via intraarticular injection to a joint of the individual. The injectable formulation may be administered in one or more injections. The formulations may be administered multiple times (e.g., up to ten times), such as, for example, once every 10 days or longer.

The steps of the method described in the various embodiments and examples disclosed herein are sufficient to carry out the methods of the present disclosure. Thus, in an embodiment, the method consists essentially of a combination of the steps of the methods disclosed herein. In an embodiment, the method consists of such steps.

The following Statements describe various non-limiting examples of the present disclosure:

Statement 1. A formulation (e.g., an injectable formulation) comprising saline and one or more liposomes, wherein the one or more liposomes are unilamellar, wherein the liposome lamella comprise 70 to 100% by mass sphingomyelin and when there is less than 100% by mass sphingomyelin the remainder is (e.g., up to 30% by mass) 1,2-dimyristoyl-sn-glycero-3-phosphocholine (DMPC) or 1,2-dimyristoyl-sn-glycero-3-phosphorylglycerol (DMPG) or DMPC and DMPG together, where the liposomes (a) have a diameter of 250 nm or less (e.g., 50 nm to 250 nm, 150 nm to 250 nm, 100 nm to 200 nm, 125 to 225 nm, 100 nm to 250 nm, 100 nm to 225 nm, 180 nm to 220 nm, or about 200 nm); (b) encapsulate adenosine in the aqueous compartment of the liposome. One or more of the liposomes have a diameter of 50 nm to 100 μm; and (c) the liposomes have an encapsulation efficiency of at least 4%. In various examples, the concentration of adenosine is 3 mg/mL.

Statement 2. A formulation (e.g., an injectable formulation) according to Statement 1, where the liposomes have a diameter of about 200 nm.

Statement 3. A formulation (e.g., an injectable formulation) according to Statement 1, where the adenosine or a portion thereof is released for up to two weeks or upon administration to a joint of an individual, the adenosine or a portion thereof is released for up to two weeks.

Statement 4. A formulation (e.g., an injectable formulation) according to any one of the preceding Statements, further comprising an excipient.

Statement 5. A formulation (e.g., an injectable formulation) according to any one of the preceding Statements, where the adenosine concentration is 0.1 to 7 mg/mL.

Statement 6. A formulation (e.g., an injectable formulation) according to Statement 5, where the adenosine concentration is 0.1 to 4 mg/mL.

Statement 7. A formulation (e.g., an injectable formulation) according to any one of the preceding Statements, where the ratio of DMPC and DMPG is from 6 to 4 to 8 to 2.

Statement 8. A formulation (e.g., an injectable formulation) according to Statement 7, where the ratio of DMPC and DMPG is 7 to 3.

Statement 9. A formulation (e.g., an injectable formulation) according to any one of the preceding Statements, where the total lipid concentration is 7 to 200 mg/mL.

Statement 10. A formulation (e.g., an injectable formulation) according to any one of the preceding Statements, where the liposomes are formed via extrusion.

Statement 11. A formulation (e.g., an injectable formulation) according to any one of the preceding Statements, where adenosine is released within 1 second to 1 hour of administration (e.g., within 1 minute to 1 hour) to the joint of the individual.

Statement 12. A formulation (e.g., an injectable formulation) according to Statement 11, where at least a portion of the adenosine is released within 1 second to 1 hour of administration (e.g., within 1 minute to 1 hour) to the joint of the individual.

Statement 13. A formulation (e.g., an injectable formulation) according to Statement 11 or Statement 12, where at least 1 to 20% of the adenosine is released 1 second to 1 hour of administration (e.g., within 1 minute to 1 hour) to the joint of the individual.

Statement 14. A formulation (e.g., an injectable formulation) according to any one of Statements 11-13, where the at least a portion of the adenosine or the at least 1 to 20% of adenosine is released within 1 second, 5 seconds, 10 seconds, 20 seconds, 30 seconds, 40 seconds, 50 seconds, 1 minute, 2 minutes, 3 minutes, 4 minutes, 5 minutes or 10 minutes of administration to the joint of the individual.

Statement 15. A method of inducing cartilage regeneration and/or treating osteoarthritis in an individual in need of treatment, comprising administering to the individual a therapeutically effective amount of a formulation (e.g., injectable formulation) according to any one of the preceding Statements.

Statement 16. A method of alleviating joint pain in an individual in need of treatment, comprising administering to the individual the formulation (e.g., injectable formulation) according to any one of Statements 1-14.

Statement 17. A method of slowing, arresting, and/or reversing progressive structural tissue damage associated with osteoarthritis in an individual in need of treatment, comprising administering to the individual the formulation (e.g., injectable formulation) according to any one of Statements 1-14.

Statement 18. A method according to any one of Statements 15-17, where the formulation (e.g., injectable formulation) is administered via intra-articular injection to a joint of the individual.

Statement 19. A method according to any one of Statements 15-18, where the injectable formulation is administered in one or more injections.

Statement 20. A method according to any one of Statements 15-19, where the injectable formulation is administered multiple times (e.g., up to 10 times) once every 10 days.

Statement 21. A method according to any one of Statements 15-20, where the individual has osteoarthritis, rheumatoid arthritis, acute gouty arthritis, and/or synovitis.

Statement 22. A method according to any one of Statements 15-21, where the individual is a human or non-human mammal. Examples of non-human mammals include, but are not limited to, agricultural animals (e.g., farm animals), such as cows, hogs, sheep, and the like, as well as pet, service, or sport animals such as horses, dogs, cats, and the like. Additional non-limiting examples of individuals include rabbits, rats, and mice.

The following examples are presented to illustrate the present disclosure. They are not intended to be limiting in any matter.

Example 1

This example provides a description of liposomes of the present disclosure.

Because adenosine has a half-life of mere seconds, the liposomal-adenosine used for the above research was made fresh daily. A series of shelf-stable formulation options based on lipid constituents, solubility efficiency and retention properties were developed and evaluated. It was determined if cholesterol/stabilizing agents should be included, and optimized the variables. The percentage of liposomal-bound adenosine in the total formulation, which can be increased or reduced by reducing or increasing the amount of adenosine solution used to hydrate the fixed amount of pre-liposomal lyophilate, was measured. The fraction of adenosine versus (adenosine+lipid) in the resulting pellet of the liposomes that form from hydrating the pre-liposomal lyophilate with the adenosine solution is dependent on the concentration of adenosine in the solution not the volume used.

All formulations hydrated with water containing 7 mg/ml of Adenosine.

| Conditions | Formulations | | | | | |
|---|---|---|---|---|---|---|
| | RgnA02 | RgnA03 | RgnA04 | RgnA05 | RgnA06 | RgnA07 |
| mg lipid | 400 | 300 | 200 | 100 | 125 | 80 |
| % SM | 0% | 25% | 50% | 75% | 75% | 100% |
| % PC/PG Mixture | 100% | 75% | 50% | 25% | 25% | 0% |
| % DMPC | 70.0% | 52.5% | 35.0% | 17.5% | 17.5% | 0.0% |
| % DMPG | 30.0% | 22.5% | 15.0% | 7.5% | 7.5% | 0.0% |
| SM (mg) | 0.00 | 75.00 | 100.00 | 75.00 | 93.75 | 80.00 |
| DMPC (mg) | 280.00 | 157.50 | 70.00 | 17.50 | 21.88 | 0.00 |
| DMPG (mg) | 120.00 | 67.50 | 30.00 | 7.50 | 9.38 | 0.00 |
| Hydrated with | 10 | 10 | 10 | 10 | 10 | 10 |

-continued

| Conditions | | | | | | |
|---|---|---|---|---|---|---|
| | Formulations | | | | | |
| | RgnA02 | RgnA03 | RgnA04 | RgnA05 | RgnA06 | RgnA07 |
| ADO Soln (ml) | | | | | | |
| Lipid in solution (mg/ml) | 40 | 30 | 20 | 10 | 12.5 | 8 |
| data analysis | | | | | | |
| [lipid] mg/ml | — | 30 | 20 | 10.0 | 12.5 | 8.0 |
| lipid amount | — | 92.4 | 36.4 | 30.8 | 53.8 | ** |
| bound ADO amount | — | 5.2 | 5.0 | 5.2 | 16.6 | ** |
| ADO/lipid in pellet | — | 6% | 14% | 17% | 31% | 18% |
| pellet/total suspension | — | 24% | 39% | 24% | 55% | |
| Dissolution time & diluent volume | Took 20 dissolve mL and more time to dissolve. | More than 10 mL to dissolve. Eventually didn't dissolve. | Overnight dissolution. | Dissolved in less than 5 min. | Overnight dissolution. | Dissolved in less than 5 min. |

Two formulations, RgnA09 (75% sphingomyelin, 17.5% DMPC, 7.5% DMPG) and RgnA10 (100% sphingomyelin) where tested in order to assess their ability to incorporate and release adenosine over time. Liposome were formed in sterile glass vials containing 100 mg of phospholipid powder. Liposomes were mixed with 10 mL of sterile adenosine solution (3 mg/ml, in saline) provided in pre-filled plastic syringes. Samples of the Lipo-adenosine suspension (100 μL) were incubated in phosphate buffer saline for 0, 1 hour, 2 hours, 1 day and 2, 5, 7, 10 days at 37° C. At the end of each incubation time, samples where centrifuged at 23,000 g for 15 min at 4° C. Supernatant was removed and the liposome pellet was re-suspended in a saline solution containing 0.5% Triton-X100. Adenosine concentration in the remaining intact liposomes was quantified by High Performance Liquid Chromatography (HPLC).

Figure 4:
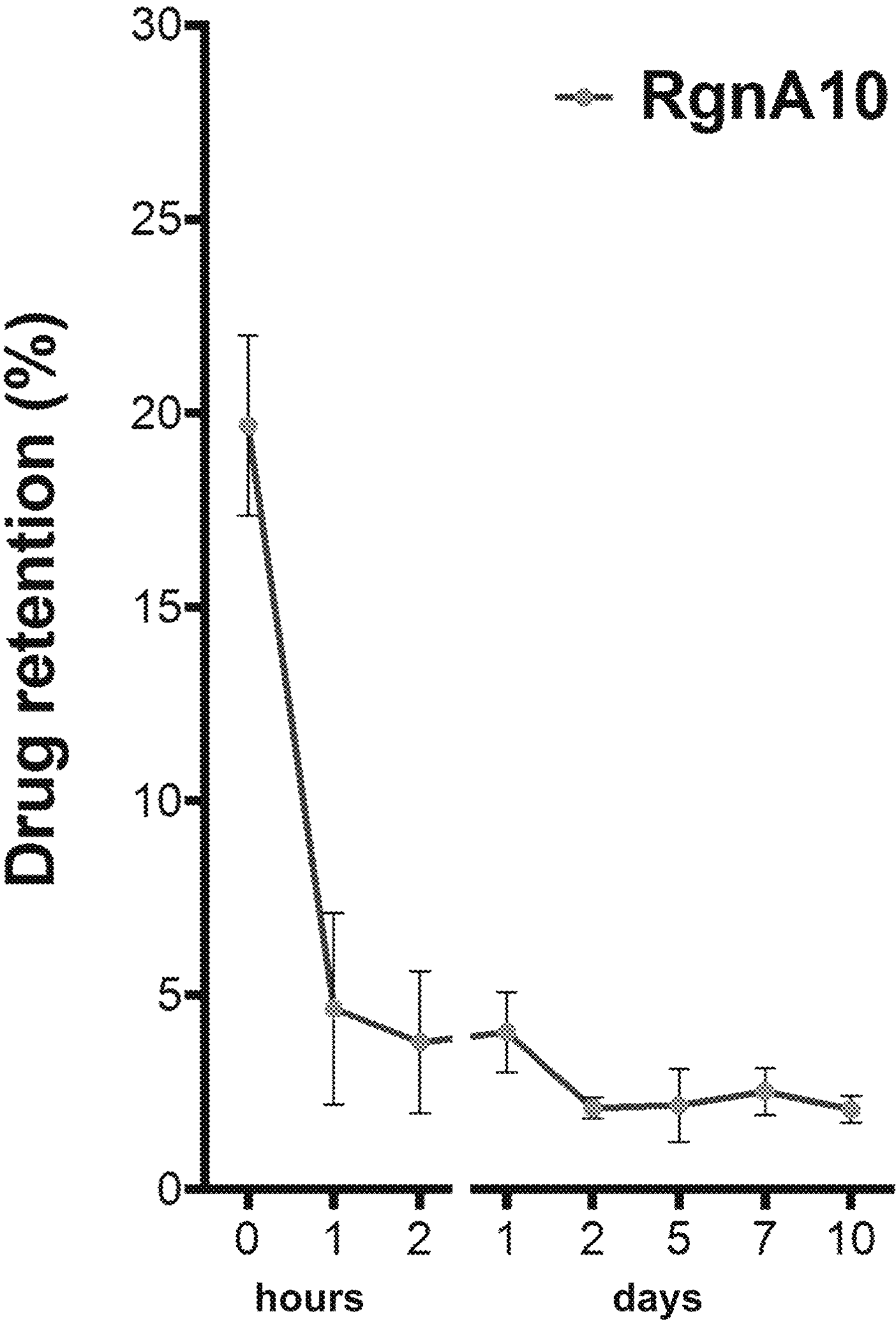
FIG. 4 shows adenosine retention of liposomes formed from RgnA10.

FIGS. 1 and 4 show the percentage of adenosine retention in both liposomal formulations. No significant difference has been detected between the RgnA09 and RgnA10. A slight higher retention was observed at time-point zero, and an increase of retention at the longer time point for the RgnA09. Freshly prepared liposome suspension (time 0) showed a retention of adenosine of 21% and 19% respectively for RgnA09 and RgnA10. The retention percentage after 1 hour of incubation drop at 4% for both formulations and slowly decrease over time reaching 1.4% and 2% (RgnA09 and RgnA10 respectively) at day 10, corresponding at 159 μM and 227 μM of adenosine.

These results show that both liposomal formulations are a good reservoir for encapsulation and slow release of adenosine in concentrations sufficient to activate A2A adenosine receptor in vivo.

The pre-liposomal lyophilate that can be rehydrated in a concentrated solution of a hydrophilic pharmacologic agent such as adenosine. In the process of said rehydration, multi-lamellar liposomal particles are created that contain said hydrophilic agent in the liposome's aqueous compartment. Said particles are "large," approximately 30 microns and are meta-stable such that they collapse into a dense form in a hyperthermic environment, approximately 40° C. Otherwise, these particles effectuate a sustained release of said pharmacologic agent if when constrained to a local closed compartment, such as within the bursa of the synovial joint of a human knee. Therefore, contained the hydrophilic agent is protected from catabolic enzymes within the physiologic environment.

The pre-liposomal lyophilate that produces these large metastable multilameller lipid particles can be manufactured by dissolving lipids (including at least 50% sphingomyelin) and up to 50% non-sphingolipid phosphatidyl choline in a mixture of water-tertiary butyl alcohol (60:40 v/v) prior to lyophilization. 1,2-dimyristoyl-sn-glycero-3-phosphocholine (DMPC) and 1,2-Dimyristoyl-sn-glycero-3-phosphorylglycerol (DMPG) were used as the non-sphingolipids in a ratio of 70% to 30%.

Example 2

This example provides a description of liposomes of the present disclosure.

Figure 8:
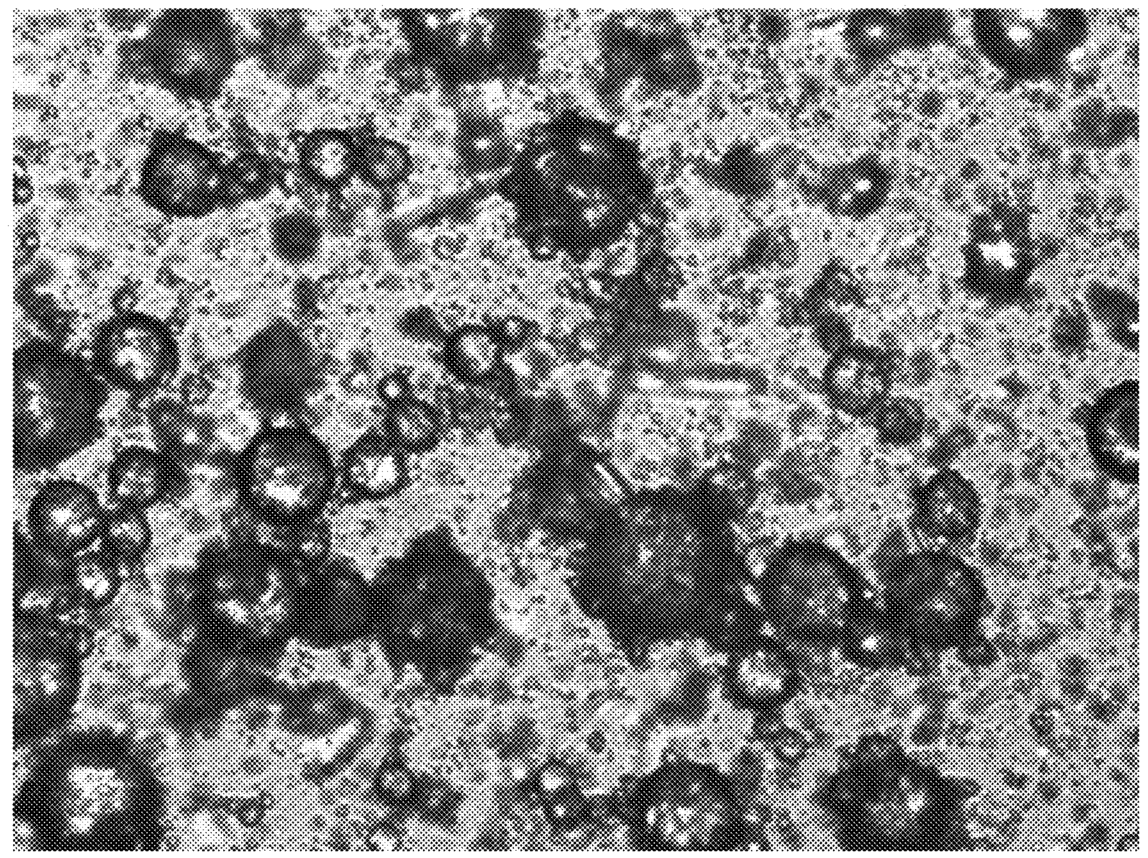
FIG. 8 shows a microscopy image of prior art liposomal suspensions. The liposomal suspension contains evidence of significant crystalized adenosine and it is believed the spherical objects are oil.

The laboratory formulations of liposomal-adenosine provided were analyzed using cross-polarized microscopy. These results are shown in FIG. 8.

The liposomal suspension, when observed microscopically, displayed evidence of significant crystalized adenosine. It is considered that this liposomal suspension may not contain significant liposomal content and is predominantly an emulsion. The spherical objects in the image are likely oil. The ingredients of this formulation contained a significant percentage (60%) of soybean oil, which would not be a component of a liposome formulation, but would be a component of an emulsion.

The solubility of adenosine in water was considered, which is 7 mg/mL. The laboratory formulation required 300 mg of adenosine to be added to 10 mL of saline. Presumably, only 70 mg of the adenosine would dissolve, leaving 230 mg of adenosine in crystalline form. It is considered that much of the pellet, when subjecting the emulsion to centrifugation, is likely to be crystalline adenosine. The pellet of the provided formulation was not by HPLC, because each time the pellet was washed, it would reduce in size until there was nothing left. The publication where this formulation was used was reviewed, and only the supernatant was analyzed by HPLC. That publication stated 73% of adenosine was retained in the liposomes. However, the amount in the pellet was inferred by measuring the concentration of adenosine in the supernatant. However, this HPLC measurement of the supernatant is consistent with 70 mg of adenosine dissolving in 10 mL of saline by its maximum solubility in water, and the remaining 230 mg of adenosine crystalized in the pellet. Presumably there are some liposomes formed with adenosine, but their presence is uncertain in this formulation.

Figure 7:
FIG. 7 shows a pre-liposomal lyophilate.

The analysis of a pre-liposomal lyophilate technique was resumed for preparing liposomal adenosine to explore the amount of adenosine capture. The advantage of this technique is that it is a stable and sterile process, ideal for pharmaceutical preparation. This technique involves the reconstitution of the sterile pre-liposomal lyophilate in the presence of the active agent. A photograph of the pre-liposomal lyophilate is shown in FIG. 7.

Figure 5:
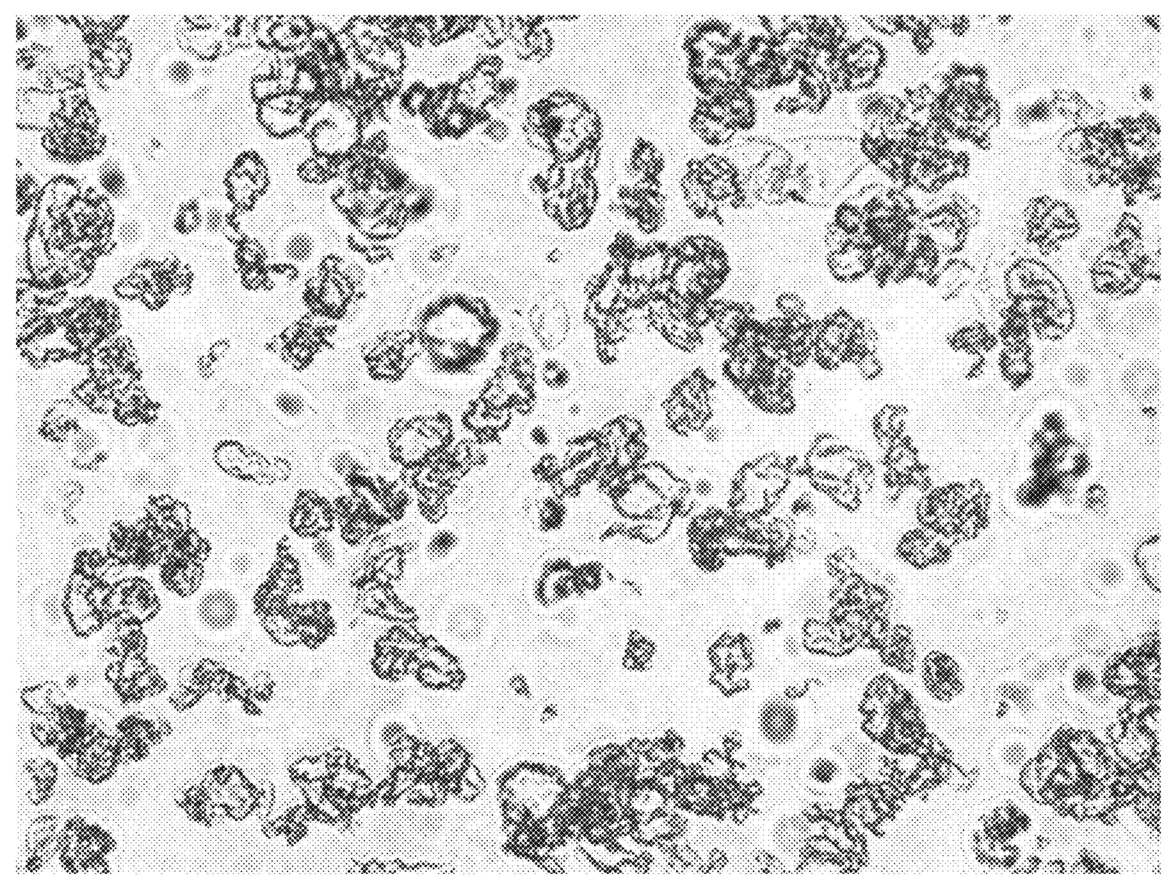
FIG. 5 shows a microscopy image of a liposomal suspension formed from RgnA10.
Figure 6:
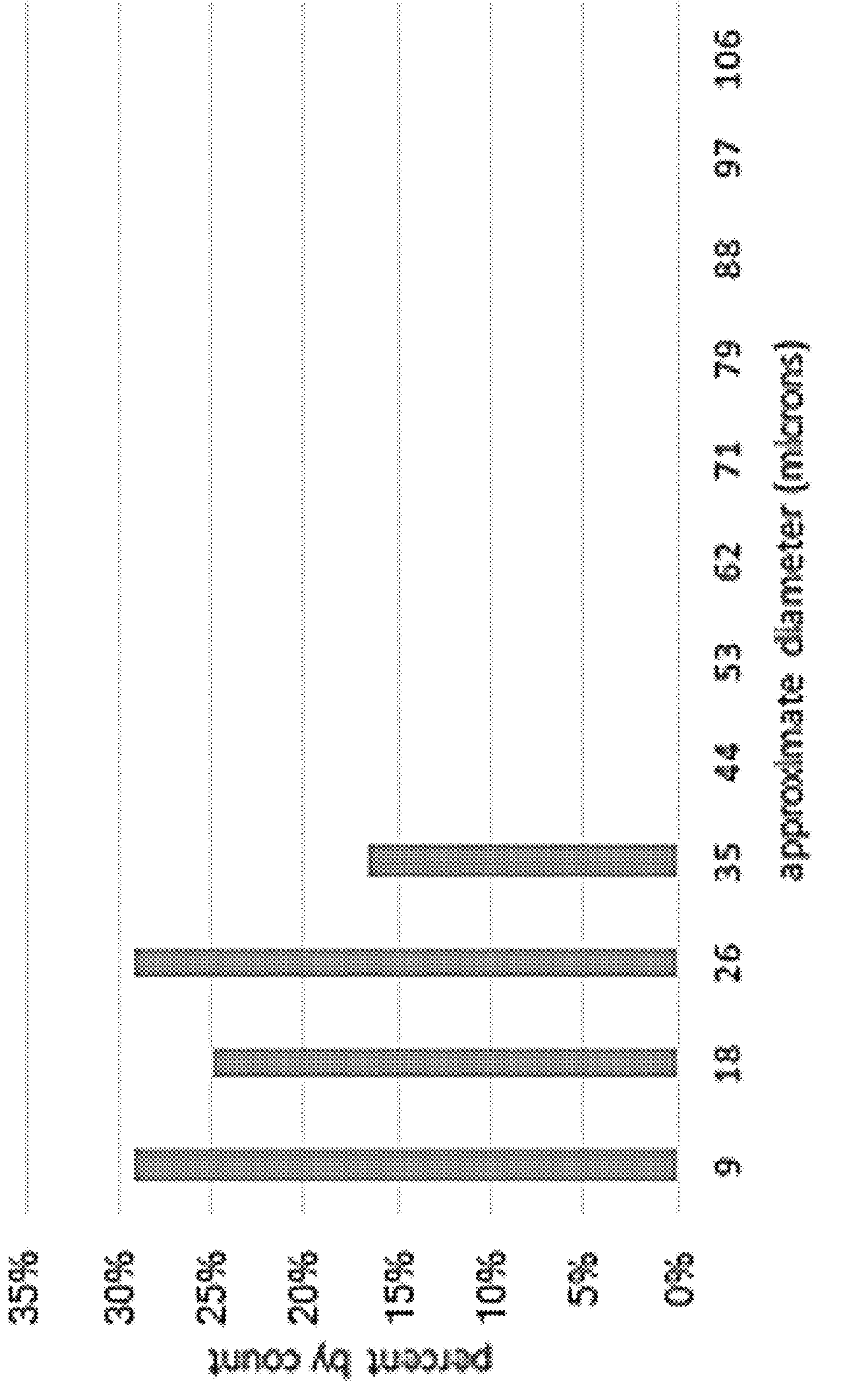
FIG. 6 shows a histogram of the approximate diameter of liposomes formed from RgnA10.

The pre-liposomal lyophilate appears as a white fluffy powder in a sterile vacuum vial. The process for rehydrating involves injecting a solution of concentrated adenosine into the vial. The powder then dissolves within 30 seconds, sometimes instantaneously, and may require gently swirling. The resulting liposomal suspension can then be removed from the vial via a syringe. Note that since the content of the vial is under vacuum, the adenosine solution will be quickly taken up by the vial upon insertion of the syringe. The ideal concentration of adenosine solution to use for rehydration is its maximum solubility in water, 7 mg/mL. For the diluent, sterile water for injection (SWFI) was used, but saline and buffered solutions can be used as well. A microscopic view of the resulting liposome suspension is shown in FIG. 5.

The average diameter of each particle is approximately 50 micrometers. In this example, we rehydrated 80 mg of powder in 11 ml of 7 mg/ml adenosine solution (in SWFI). Note that the microscopy image above is a dilution to be able to allow the viewing of separate liposomal particles.

Figure 10:
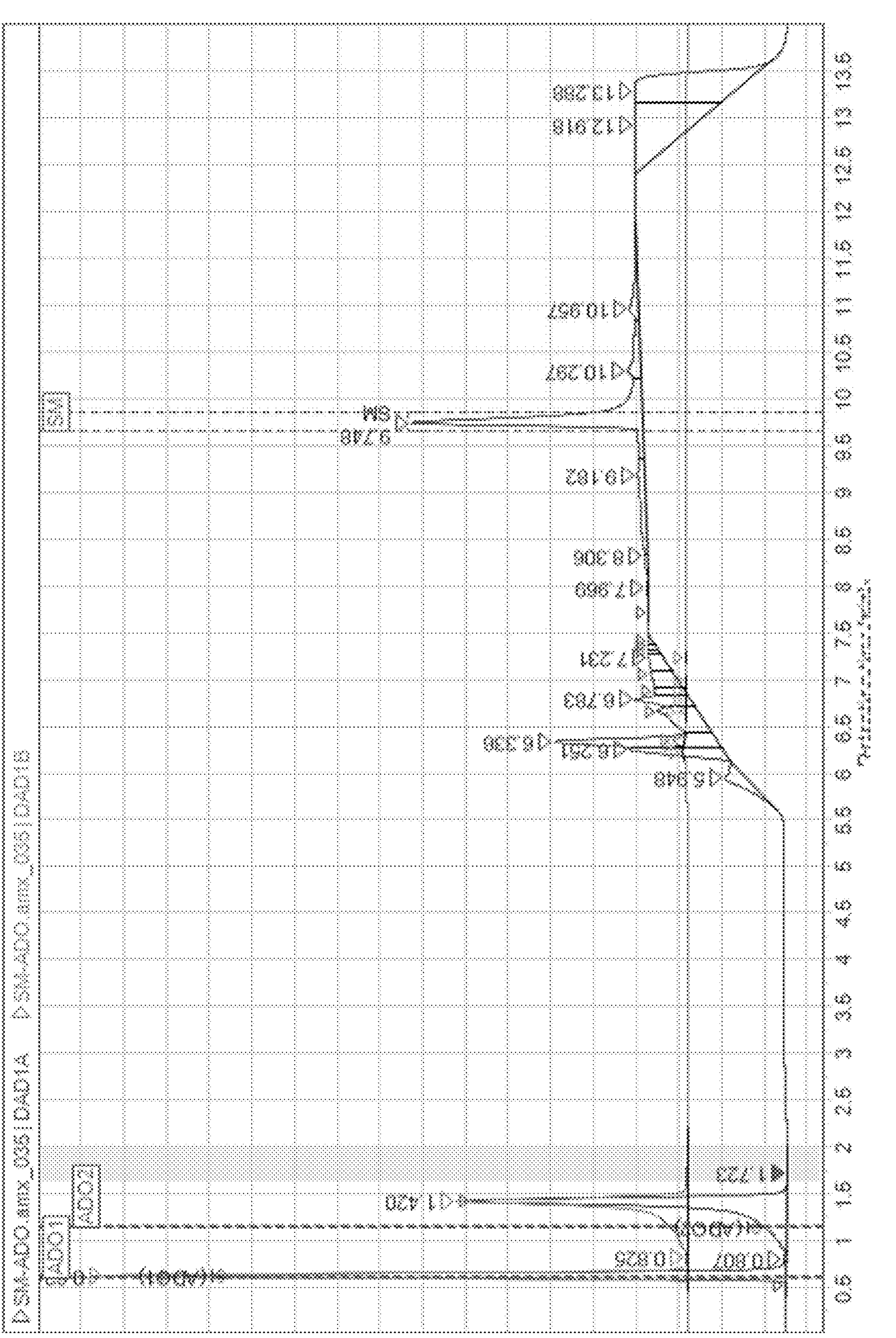
FIG. 10 shows an HPLC chromatogram of material isolated in Example 1.

An HPLC method for measuring both adenosine and lipid content was prototyped. The liposome formulation was subjected to centrifugation, and the pellet was separated from the supernatant. Complete dissolution of the pellet was obtained with methanol. The lipid portion of the liposome was relatively insoluble in acetonitrile, whereas adenosine is soluble in acetonitrile. Therefore, the HPLC method involved an initial mobile water/acetonitrile phase that first eluted adenosine from the HPLC column (which was a C18 column), followed by a methanol mobile phase to elute the lipid. One standard for each agent was run: adenosine and lipid. The dissolved pellet was run and compared the result to those standards. The pellet chromatogram is shown in FIG. 10.

Figure 11:
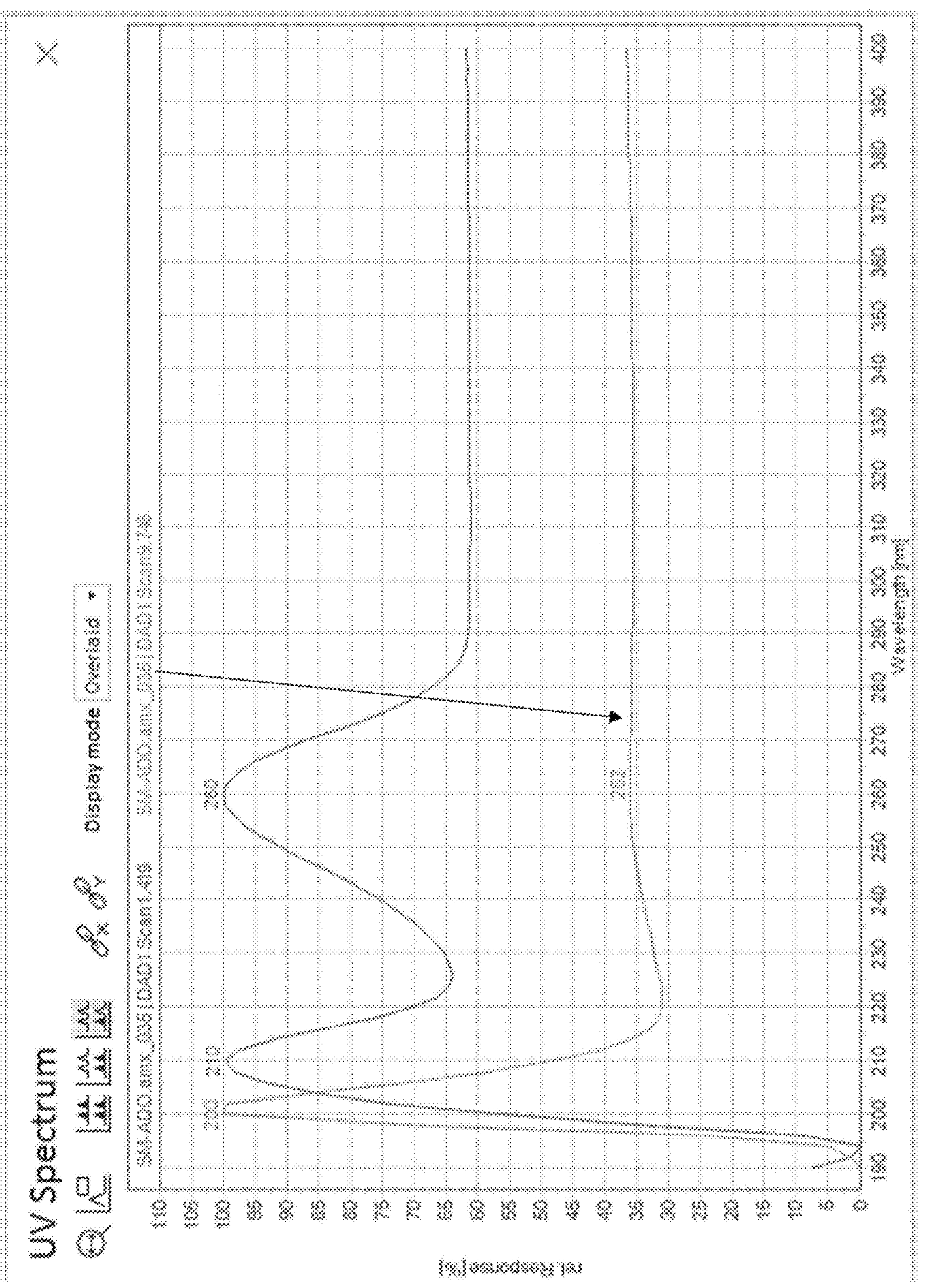
FIG. 11 shows the UV spectrum of the material isolated in FIG. 10.

The retention time of adenosine in this method is 1.42 minutes, and the retention time of the lipid is 9.75 minutes. The two analytes are also detected at different wavelengths: 260 nm and 203 nm for adenosine and lipid respectively. The FIG. 11 shows these spectra.

The lipid [SM] standard was 4 mg/mL and the adenosine [ADO] standard was 1 mg/ml. The resulting peak areas for the standard runs were as follows.

| SM | ADO |
|---|---|
| 22,521 | 25,783 |
| 22,317 | 25,072 |
| 22,558 | 25,158 |
| 22,465 | 25,338 |

In lieu of a calibration curve, the following was considered:

[SM]=SM/22,465/4=SM/5,616

[ADO]=ADO/25,338

The pellet was then run in triplicate, and the following results were obtained for the two peaks.

| INDEX | ADO | SM |
|---|---|---|
| 1 | 8046 | 7157 |
| 2 | 8320 | 8387 |
| 3 | 8318 | 9764 |

The fraction of adenosine in the pellet (defined as [ADO]/([ADO]+[SM])) as a function of the ratio of chromatogram peak areas (ADO/SM) can be derived as follows:

$$[ADO] = ADO/25{,}338$$

$$[SM] = SM/5616$$

$$\frac{[ADO]}{[SM]} = \frac{ADO}{SM}0.2216$$

$$\frac{[ADO]}{[ADO]+[SM]} = \frac{[ADO]/[SM]}{[ADO]/[SM]+[SM]/[SM]} = \frac{[ADO]/[SM]}{[ADO]/[SM]+1}$$

$$\frac{[ADO]}{[ADO]+[SM]} = \frac{\frac{ADO}{SM}0.2216}{\left(\frac{ADO}{SM}0.2216\right)+1}$$

When applied to the chromatogram results, the following values were obtained:

| INDEX | ADO | SM | ADO/SM | [ADO]/([ADO] + [SM]) |
|---|---|---|---|---|
| 1 | 8046 | 7157 | 1.124214056 | 19.94% |
| 2 | 8320 | 8387 | 0.992011446 | 18.02% |
| 3 | 8318 | 9764 | 0.851904957 | 15.88% |
| | | | | 17.95% |

Example 3

This example provides a description of methods of use of injectable formulations of the present disclosure.

Rats with established OA received an intra-articular injection of saline (100 μL) and other 8 groups of animals received Ade in 2 different liposomal formulations at the doses of, 3, 1, 0.3 and 0 mg/mL. The first injection was performed 4 weeks after the ACL rupture. Animals received one injection every 10 days, 6 times. Knee swelling was measured before every injection as a measure of articular inflammation. Pain test was performed in rats at baseline (before the first injection), 5 days after the 3$^{rd}$ injection and finally at 57 days, right before sacrifice (7 days after the last injection). Post-sacrifice joints was analyzed using histology and uCT.

10 treatment groups 2 formulations×4 doses=8 treatment groups 1 positive control (Rgn01)

1 negative control (saline)

RgnA01 was prepared as described in Corciulo et al., Endogenous adenosine maintains cartilage homeostasis and exogenous adenosine inhibits osteoarthritis progression, Nat Commun. 2017 May 11; 8:15019. The concentration of adenosine in these liposomes is 2.7 mg/mL.

Liposomes were prepared fresh the day before injection. Ethanol was added to soybean oil containing adenosine, or adenosine plus adenosine receptor antagonists. The lipid phase containing phosphatidyl choline and cholesterol (1:0.5 by molar ratio) was added to the previous solution and emulsified at 15,000 r.p.m. for 10 min. Saline along with glycerin was then added to the lipid phase and was homogenized at 15,000 r.p.m. for 20 min followed by sonication for 1 min at 100% duty cycle.

PTOA rats were randomized to experimental groups. Pain tests were performed before the beginning of the experiment (4 weeks after the ACL rupture) and 5 days after the 3rd injection. Pain behavior was measured as weight bearing asymmetry between the ipsilateral and contralateral hind limbs using an incapacitance meter. After the hyperalgesia test animals were placed in a rodent restrainers to let them stand on their hind paws. Hind limbs were resting on the two weight averaging platform pads. As the animal shifts their weight from each pad, the unit recorded the average weight in grams over 12 seconds for 3-4 consecutive measurements. The mean value for each animals was used for the statistical analysis.

Example 4

This example provides a description of methods to prepare liposomes of the present disclosure and release kinetics of liposomes of the present disclosure.

Preparation of Pre-Liposomal Lyophilate:

| Conditions | | |
|---|---|---|
| Formulations | RgnA09 | RgnA10 |
| mg lipid | 100 | 100 |
| % SM | 75% | 100% |
| % PC/PG Mixture | 25% | 0% |
| % DMPC | 17.5% | 0.0% |
| % DMPG | 7.5% | 0.0% |
| SM (mg) | 75.00 | 100.00 |
| DMPC (mg) | 17.50 | 0.00 |
| DMPG (mg) | 7.50 | 0.00 |
| Hydrated with 3 mg/ml ADO Soln (ml) | 10 | 10 |
| Lipid in solution (mg/ml) | 10 | 10 |
| Dissolution time & diluent volume | Dissolved in less than 5 min. | Dissolved in less than 5 min. |

All vials contained 100 mg total and the fill volume was 5 mL, with a fill concentration 20 mg/ml solvent.

For RgnA09, 75 mg SM, 17.5 mg DMPC, and 7.5 mg DMPG was dissolved in 5 mL of a 1:1 (ratio by volume) of a water to tertiary-butyl alcohol (TBA) mixture. This solution was lyophilized with the following parameters (first freezing at −40° C. for 30 min, then primary drying at 10° C. for 20 h under a vacuum of 200 micron, followed by secondary drying at 20° C. for 4.5 h), and maintained in a vacuum-sealed vial. The lyophilate was then rehydrated with 40 mg of pure water at room temperature (25° C.).

For RgnA10, 100 mg of pure sphingomyelin (SM) was dissolved in 5 mL of a 3:2 (ratio by volume) of a water to tertiary-butyl alcohol (TBA) mixture. This solution was lyophilized with the following parameters (first freezing at −40° C. for 30 min, then primary drying at 10° C. for 20 h under a vacuum of 200 micron, followed by secondary drying at 20° C. for 4.5 h), and maintained in a vacuum-sealed vial. The lyophilate was then rehydrated with 40 mg of pure water at room temperature (25° C.)

Preparation of Adenosine stock solution: Adenosine stock solution was prepared by dissolving pure adenosine powder into saline buffer (0.9% saline). 50 mL of 0.9% saline was transferred into a sterile centrifuge tube, then 150 mg of adenosine was weighed and transferred into the saline rendering a 3 mg/ml stock solution. The solution was mixed via intermittent vigorous vortexing over the course of at least 30 minutes. The solution was then filtered into a new 50 mL centrifuge tube with a 0.2 μm sterile syringe filter to remove large undissolved adenosine particles, yielding a solution containing monomeric dissolved adenosine. Solutions were prepared at room temperature and were stored refrigerated (2-8° C.) after use.

Preparation of liposomal-adenosine suspension. Liposome solutions were initially prepared by the following procedure, starting with glass vials containing 100 mg of lyophilized lipid powder of the appropriate composition. Each vial of lipid was then hydrated by injecting 10 mL of adenosine stock solution (3 mg/ml in saline) into the vial and vigorously vortexing. Dissolving 100 mg of lipid in 10 mL of buffer was expected to yield solutions with 10 mg/mL total lipid. The liposomes formed are expected to be multilamellar with sizes ranging from 1-10 μm, with some larger and smaller liposomes possible.

24 h In-Vitro Release by Dialysis: Preparing the dialysis cassette: dialysis cassettes were primed for use following manufacturer's recommended protocol. Briefly, the dialysis cassette was filled with 5 mL of 20% EtOH (200 proof ethanol mixed with DI water as a 1:4 v/v ratio) and allowed to float in a glass beaker containing 500 mL of 20% EtOH for 10 minutes. No stir bar or stirring was used for this step. The dialysis cassette was then emptied by pipette and filled with 5 L DI water, and the 500 mL volume was discarded and replaced with 500 mL of DI water, and the dialysis cassette was allowed to float in the DI water for another 20 minutes (no spinning). The cassette was then considered suitable for use after removing the 5 mL DI water.

Preparing the dialysis chamber: 1 L glass beakers were filled with 500 mL of 0.9% saline as the external buffer. A magnetic stir bar was added to each glass beaker.

Dialysis cassettes were filled with 3 mL of the appropriate test solution, either 1) pure adenosine stock solution, or 2) multilamellar liposome+Ade solution.

Filled dialysis cassettes were then placed in the foam float ring and allowed to float in the 500 mL of 0.9% saline, with one dialysis cassette per 500 mL container. The stir plate was adjusted to maintain even stirring, without splashing and without funnel/vortex formation that might affect the cassette, at a rotation rate of 250-300 rpm. The zero-time point was taken as the time at which the sampled-filled cassette was first placed into beaker and stirring initiated.

Samples of the retentate (the solution inside of the dialysis cassette) were taken at various timepoints by first mixing the solution inside the cassette by gentle pipetting with a 1 mL pipette, then removing 50 μL and transferring it to a pre-labelled 1.5 mL Eppendorf tube.

Analysis of adenosine concentration was performed using a NanoDrop OneC spectrophotometer to measure the UV/Vis absorbance at 260 nm (baseline correction ON at 750 nm, automated pathlength off). The measurements were all blanked against 0.9% saline. UV/Vis measurements were made using 2 μL samples pipetted onto the instrument pedestal, with a total n=3 measurements (three×2 μL volumes, cleaning the pedestal between each measurement by wiping with a lint-free wipe) per sample condition time point.

10 day In-vitro release kinetics: Liposomal lyophilates in sterile glass vials were mixed with sterile adenosine solution (3 mg/ml, in saline) provided in pre-filled plastic syringes (custom order from Mycoscience Inc). Samples of the Lipo-adenosine suspension (100 μl) were incubated in phosphate-buffered saline for 0, 1, or 2 h, and 1, 2, 5, 7, or 10 days at 37° C. At the end of each incubation time, samples were centrifuged at 23,000×g for 15 min at 4° C. Supernatant was removed, and the liposome pellet re-suspended in a saline solution containing 0.5% Triton-X100. Adenosine concentration in the remaining intact liposomes was quantified by high-performance liquid chromatography (HPLC).

Animal study: Rats with established OA received intraarticular injection of saline (100 ul) and other 8 groups of animals will receive Ade in 2 different formulations at the doses of 3, 1, 0.33 and 0 mg/ml. The first injection was performed 4 weeks after the ACL rupture. Animals received one injection every 10 days, 6 times. Knee swelling was measured before every injection as a measure of articular inflammation. Pain tests were performed in rats at baseline (before the first injection), after 30 days before the 3rd injection and finally at 57 days, right before sacrifice (7 days after the last injection). A test of pain and a motor test were performed, the incapacitance test (measured as weight bearing asymmetry between the ipsilateral and contralateral hind limbs by incapacitance meter) and the rotarod test (time that the rat was able to continue running on a rotating rod before falling off). Post-sacrifice joints will be analyzed using histology and uCT.

Figure 13:
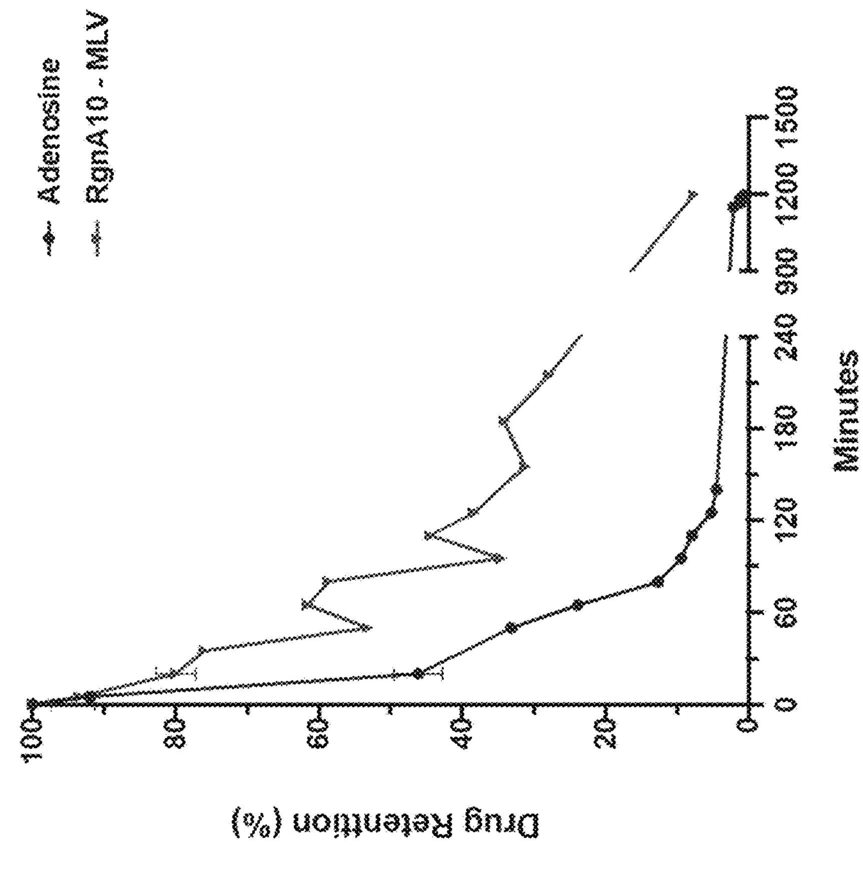
FIG. 13 shows the release kinetics of adenosine over 24 hours from (left) RgnA09-MLV and (right) RgnA10-MLV.
Figure 13:
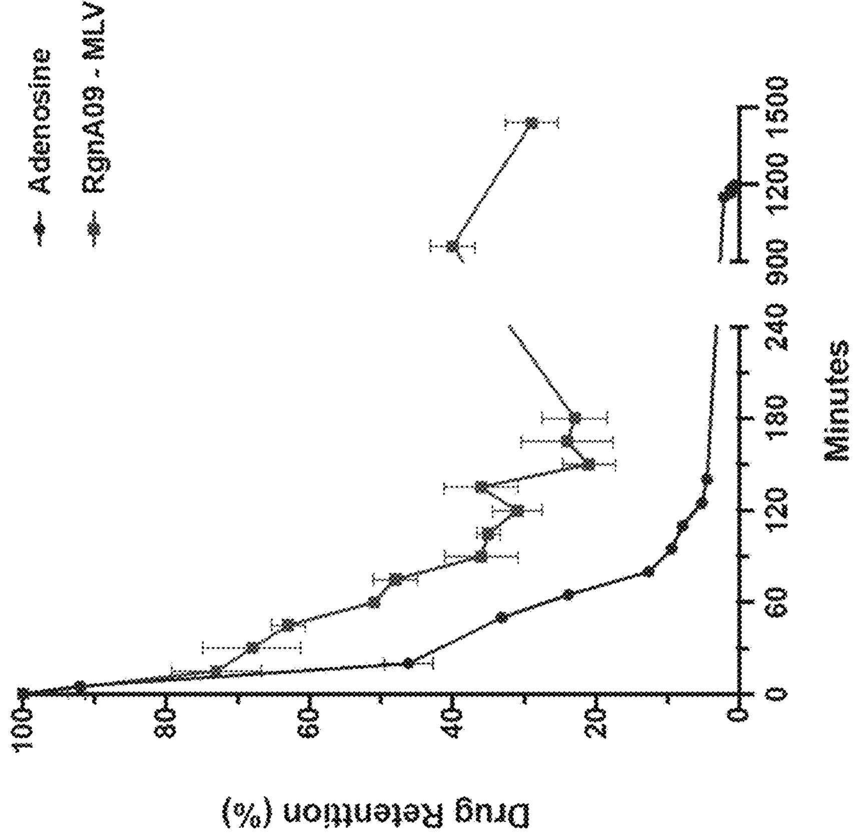

24 h In-Vitro Release by Dialysis: FIG. 13 shows that the non-liposomal adenosine is released over time. However, RgnA09 effectuates an overall 21.86% to 37.90% higher dose due to a slow release of the liposomal-adenosine due to a higher retention of the drug in liposomes and several bursts of release around 2 hrs and 16 hrs, resulting in 25.76% and 37.90% higher dose. In contrast, RgnA10 effectuates an overall 26.61% to 49.27% higher dose due to a slow release of the liposomal-adenosine due to a higher retention of the drug in liposomes and several bursts of release around 1 hr, 2 hrs and 3 hrs, resulting in 48.89%, 39.21% and 29.65% higher dose.

Figure 12:
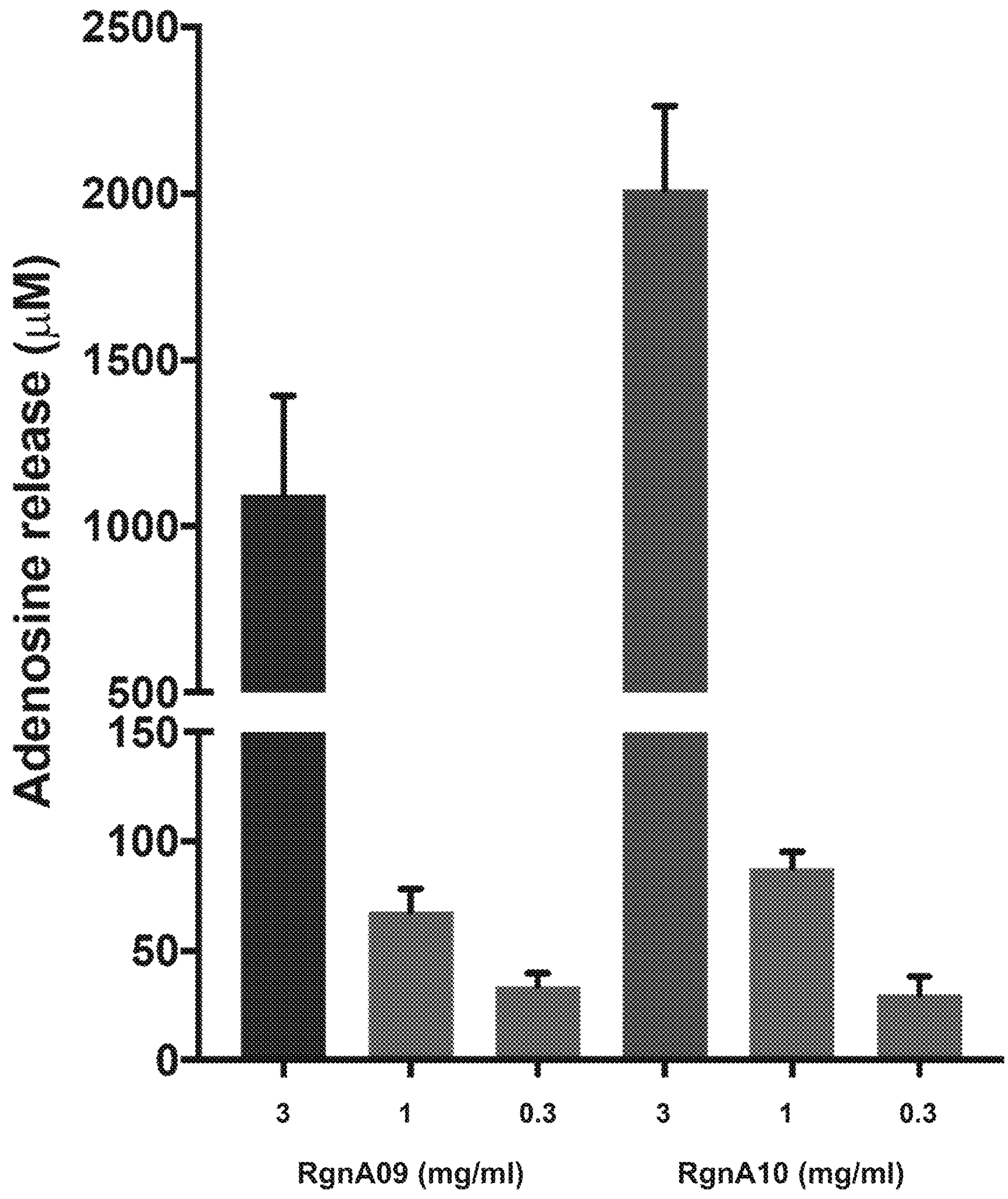
FIG. 12 shows the initial bolus release of RgnA09 and RgnA10.

10 day In-vitro release kinetics: FIG. 12 shows the percent adenosine retention in both liposomal formulations. There is an initial bolus release of adenosine (1096 μM with RgnA09; 2014 μM with RgnA10). No significant difference has been detected between RgnA09 and RgnA10 formulations. Fresh prepared liposome suspension (time 0) shows 21% retention of adenosine for RgnA09 and 19% for RgnA10. FIG. 1 and FIG. 4 show after 1 h of incubation, retention drops to 4% for both formulations, slowly decreasing over time to reach 1.4% and 2% (RgnA09 and RgnA10, respectively) at day 10, corresponding at 159 μM and 227 μM adenosine. These results show that both liposomal formulations are good reservoirs for encapsulation and slow release of adenosine in concentrations sufficient to activate A2A receptor in vivo.

Animal study: We further tested the efficacy of the newly developed formulations in the post-traumatic OA (PTOA) rat model. As described above, rats develop OA after mechanical rupture of the ACL. PTOA rats were randomized to experimental groups. Incapacitance pain tests were performed prior to beginning the experiment. Animals were divided into 10 groups, to receive RgnA09 or RgnA10 at 0 (empty liposome/vehicle), 0.3, 1, or 3 mg/ml of adenosine, saline, or formulation, as described previously in Corciulo et al. Animals received one injection every 10 days, 6 times. Knee swelling was measured before every injection as a measure of articular inflammation. Pain test was performed in rats at baseline (before first injection), at 30 days (mid-term of the treatment regimen), and right before sacrifice (7 days after the last injection). Post-sacrifice joints were analyzed using histology and uCT. Pain behavior was measured as weight bearing asymmetry between the ipsilateral and contralateral hind limbs by incapacitance meter and by the rotarod test.

Figure 9:
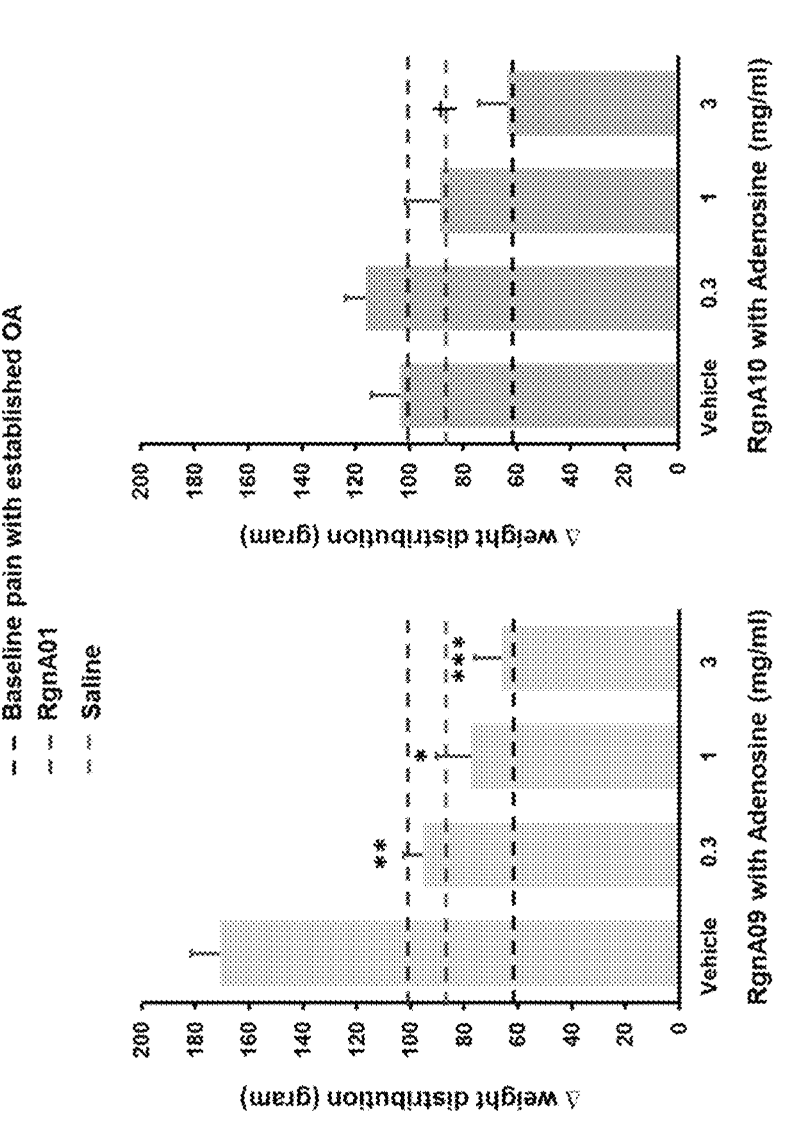
FIG. 9 shows recorded pain data using an incapacitance test.
Figure 14:
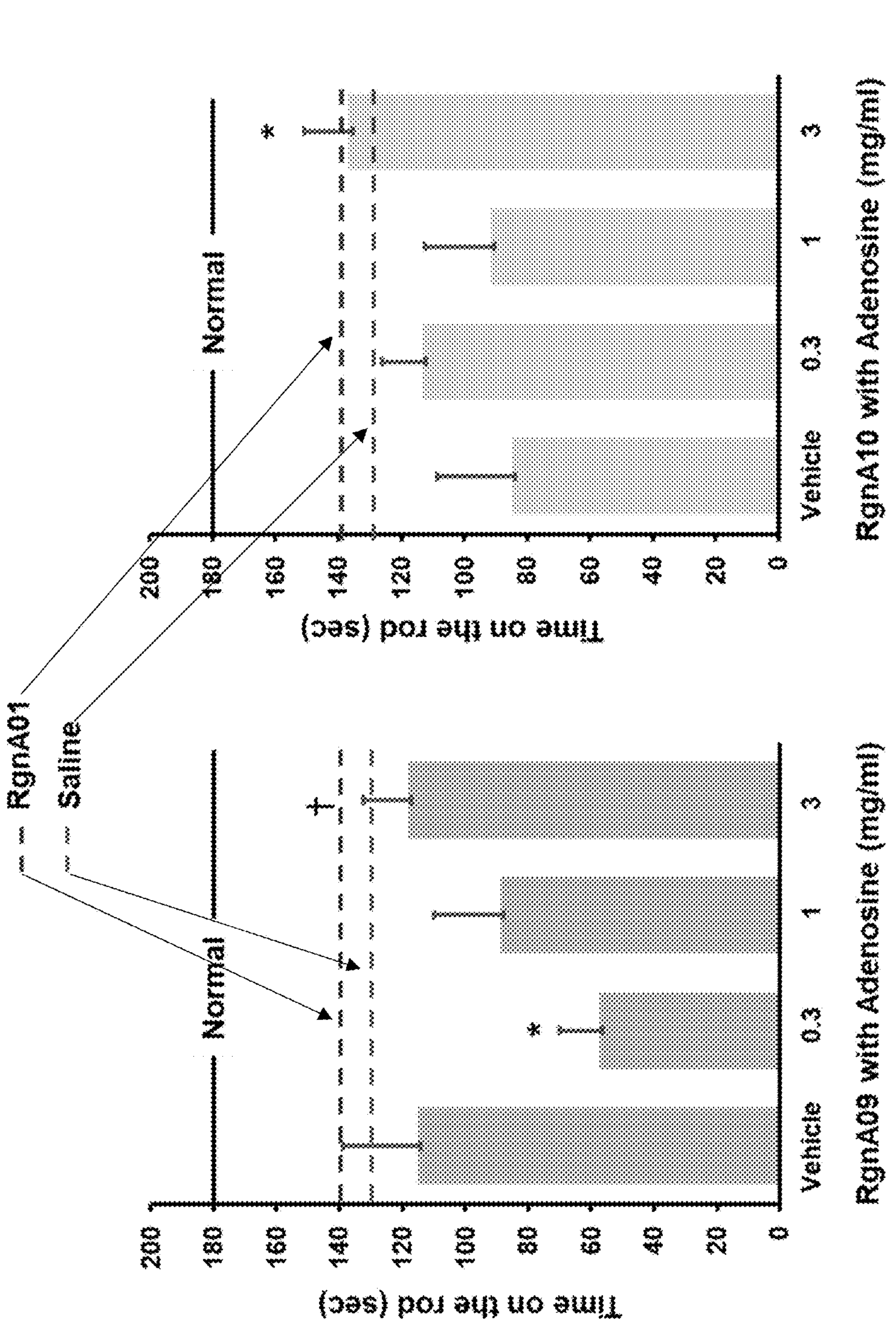
FIG. 14 shows rotarod pain test at 60 days (after six injections) with (left) RgnA09 and (right) RgnA10.
Figure 15:
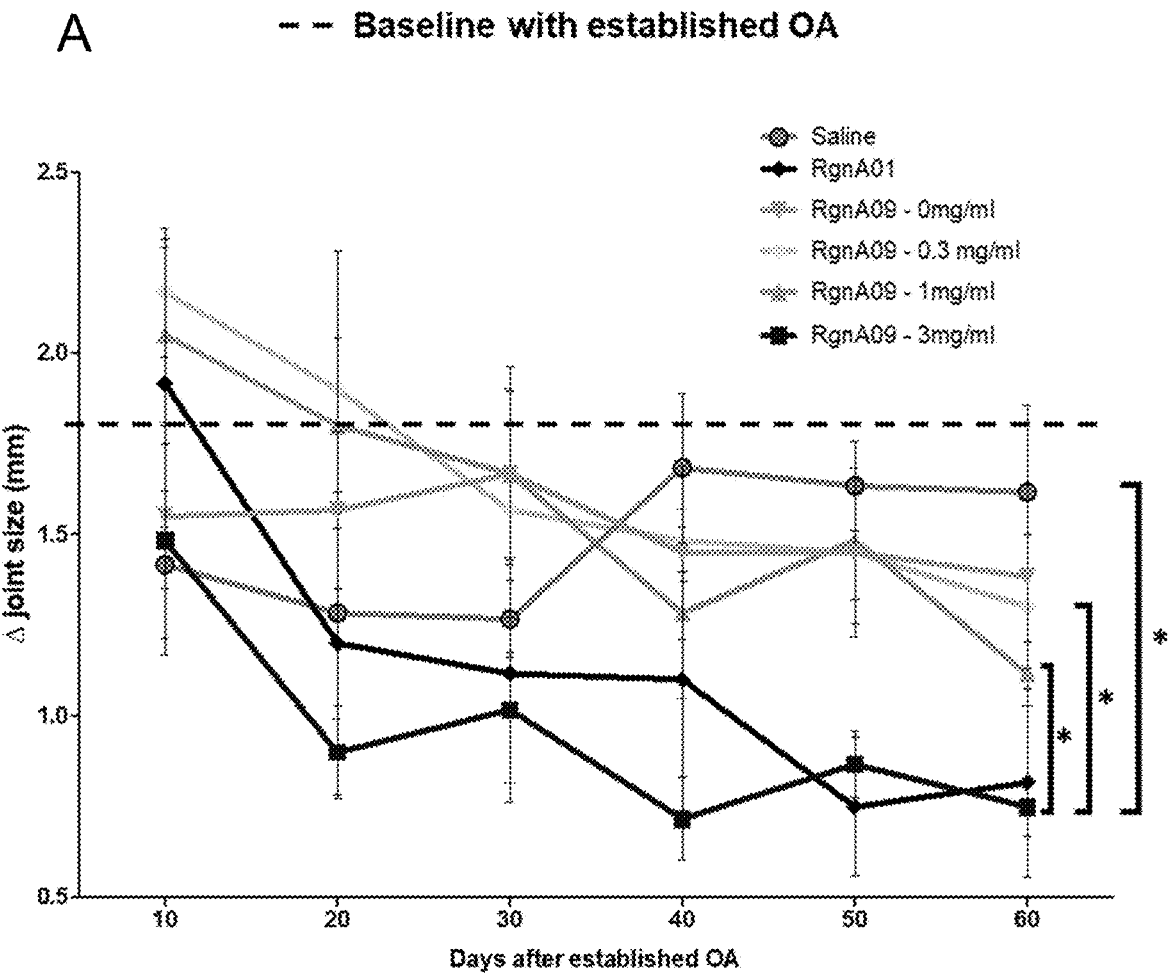
FIG. 15 shows the effect of (A) RgnA09 and (B) RgnA10 on joint inflammation at various concentrations over 6 injections. Administration was ipsilateral-contralateral. Statistics: One-way (Brown-Forsythe and Welch) ANOVA. *P<0.05 v/s vehicle, †P<0.05 v/s saline, +P<0.05 v/s 0.3 mg and 1 mg.
Figure 15:
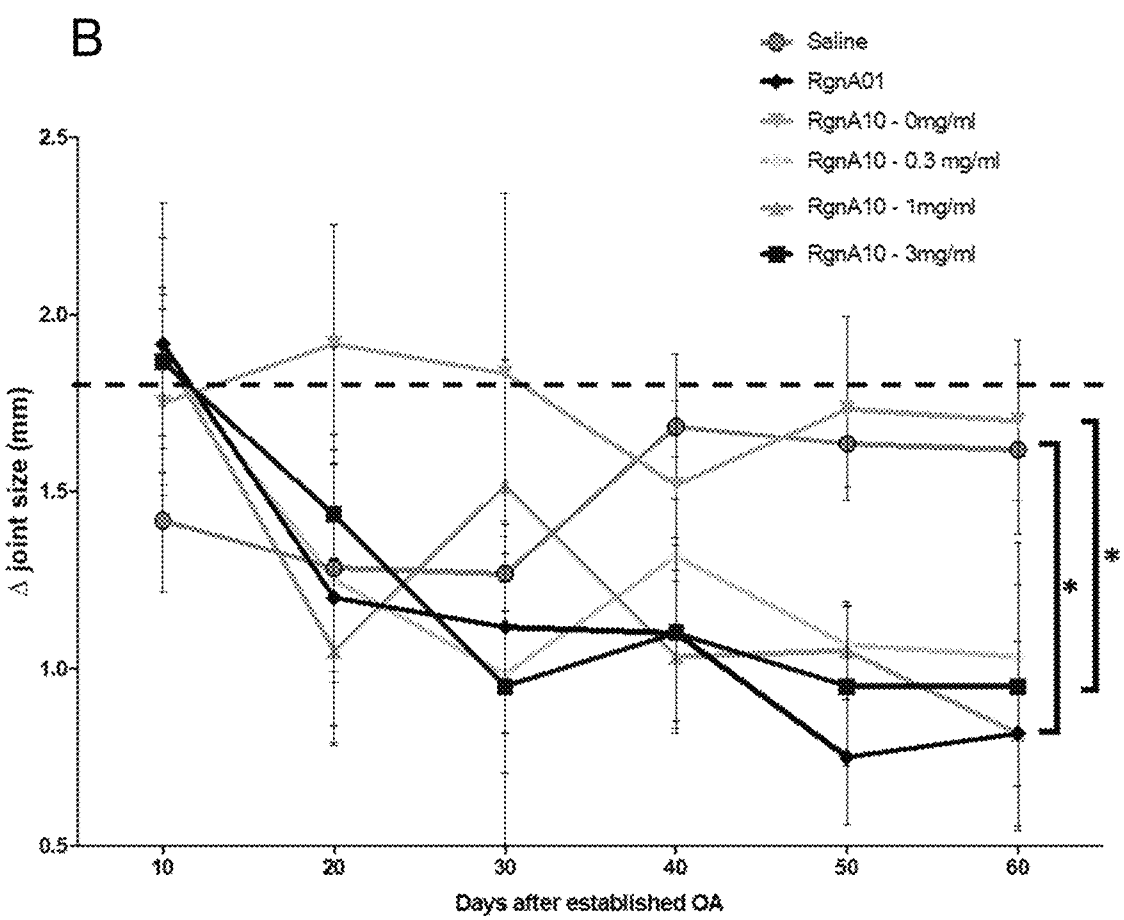

Animals were placed in rodent restrainers to stand on hind paws, with hind limbs resting on two weight-averaging platform pads. As the animal shifted their weight from each pad, the unit recorded the average weight in grams over 12 seconds for 3-4 consecutive measurements. The mean value for each animal was used for analysis. Pain was also measured using the rotarod test, which provides assessment of motor function with pressure and stress on the knee joint. Rats were placed onto an accelerating rotarod, and failure to stay atop the rod was measured and used for further analysis Based on the incapacitance test, there was a strong reduction in pain behavior between animals treated with intra-articular vehicle and 1 mg/ml for RgnA09, and between 0.3 mg and 3 mg with RgnA10. In addition, at 30 days (after 3 injections) we observed a steady trend of a dose response in the reduction of joint pain with both formulations, with all doses significantly different from vehicle for Rgn09, and 3 mg of Rgn10 different from Rgn01 and vehicle (FIG. 9). The rotarod test also showed a dose-response trend and a difference at 60 days with the highest dose of Rgn10 (3 mg/ml) (FIG. 14). In addition, we observed remarkable changes in joint inflammation with both formulations, with some doses showing significant differences to vehicle and saline after 6 injections. There was a steady decrease in joint inflammation over time with both formulations at 3 mg/ml (FIG. 15). Both Rgn09 and Rgn10 were used at the highest dose of 3 mg/ml.

Figure 16:
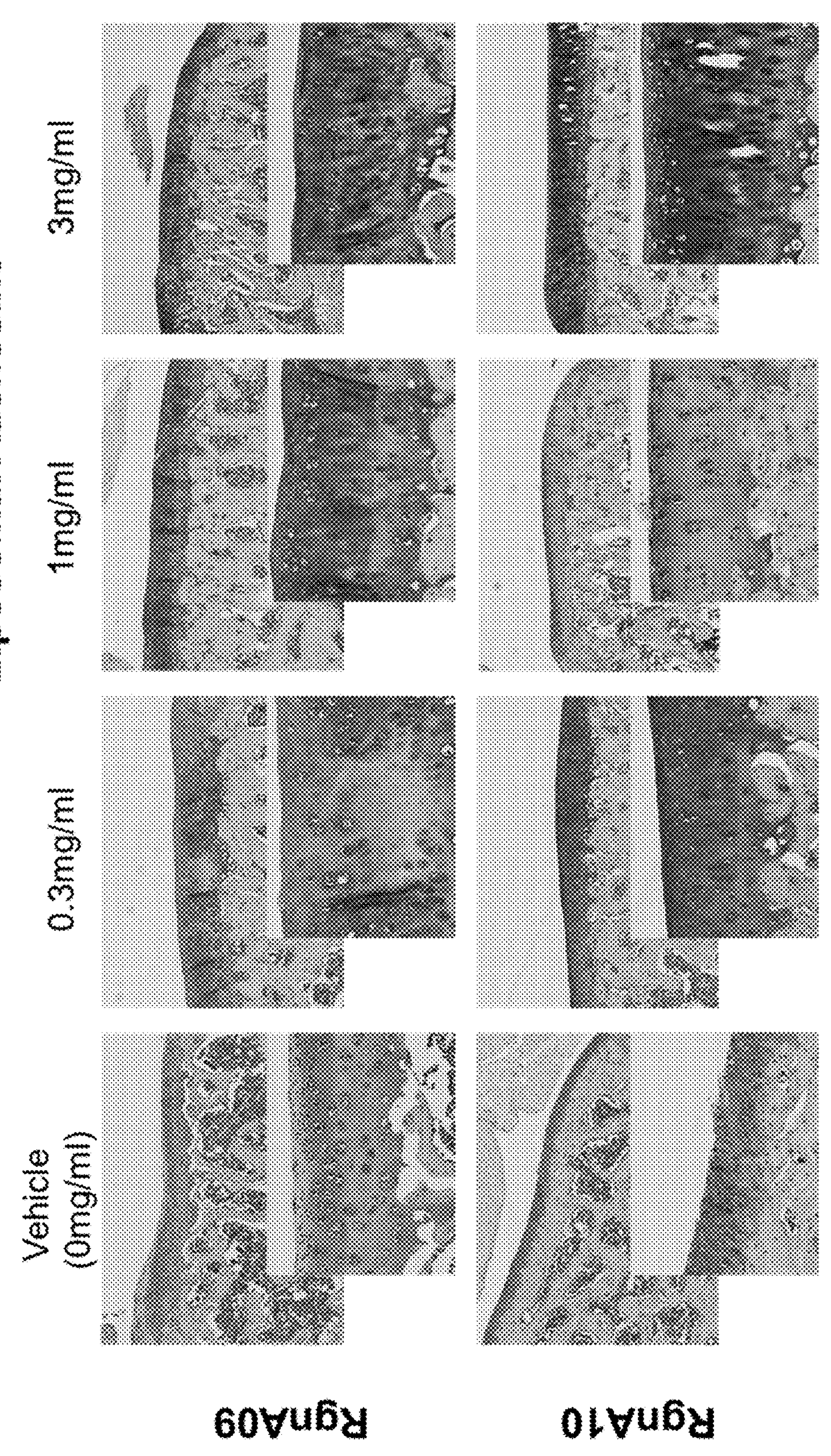
FIG. 16 shows representative safranin O-stained sections of the affected rat tibias after treatment with vehicle or 3 doses of liposomal adenosine. In the vehicle-treated animals there was a marked reduction in cartilage proteoglycan and surface irregularity of the cartilage. There was a dose-dependent improvement in cartilage proteoglycan and loss of fraying of the cartilage in the RgnA09-treated rats with increased surface cartilage. In the RgnA10-treated rats the effect was strongest in the cartilage of those treated with the highest dose studied (3 mg/ml) although preservation of the cartilage was observed at the lower doses as well.

Shown in FIG. 16 are representative safranin O-stained sections of the affected rat tibias after treatment with vehicle or 3 doses of liposomal adenosine. In the vehicle-treated animals there was a marked reduction in cartilage proteoglycan and surface irregularity of the cartilage. There was a dose-dependent improvement in cartilage proteoglycan and loss of fraying of the cartilage in the RgnA09-treated rats with increased surface cartilage. In the RgnA10-treated rats the effect was strongest in the cartilage of those treated with the highest dose studied (3 mg/ml) although preservation of the cartilage was observed at the lower doses as well.

Conclusion: The new formulations of liposomal adenosine were as effective, if not more effective, at relief of both pain and swelling in the OA knees with concomitant preservation and enhancement of cartilage. Both formulations were effective and the in vitro release of adenosine from the multilamellar vesicles was superior to the non-liposomal or free adenosine.

Example 5

This example provides a methods of using liposomes of the present disclosure.

Shelf-stable formulations RgnA09 and RgnA10. Developed and evaluated was a series of shelf-stable formulation options based on lipid constituents, solubility efficiency, and retention properties. RgnA09 and RgnA10 can be rehydrated in a concentrated solution of a hydrophilic adenosine. In the process of said rehydration, multi-lamellar liposomal particles are created that contain adenosine in the liposome's aqueous compartment. The liposomes are ~10-100 microns in size and are meta-stable, such that they collapse into a dense form in a hyperthermic environment (~40° C.). The liposomes effectuate sustained release of adenosine when constrained to a local closed compartment, such as within the bursa of the synovial joint of a human knee. RgnA09 and RgnA10 were tested in order to assess their ability to incorporate and release adenosine over time. Liposomal lyophilates in sterile glass vials were mixed with sterile adenosine solution (3 mg/mL, in saline) provided in pre-filled plastic syringes (custom order from Mycoscience Inc). Samples of the Lipo-adenosine suspension (100 μL) were incubated in phosphate-buffered saline for 0, 1, or 2 h, and 1, 2, 5, 7, or 10 days at 37° C. At the end of each incubation time, samples were centrifuged at 23,000×g for 15 min at 4° C. Supernatant was removed, and the liposome pellet re-suspended in a saline solution containing 0.5% Triton-X100. Adenosine concentration in the remaining intact liposomes was quantified by high-performance liquid chromatography (HPLC). FIGS. 1, 4, and 12 shows the percent adenosine retention in both liposomal formulations. There is an initial bolus release of adenosine (1096 μM with RgnA09; 2014 UM with RgnA10). No significant difference has been detected between RgnA09 and RgnA10 formulations. Fresh prepared liposome suspension (time 0) shows 21% retention of adenosine for RgnA09 and 19% for RgnA10. After 1 h of incubation, retention drops to 4% for both formulations, slowly decreasing over time to reach 1.4% and 2% (RgnA09 and RgnA10, respectively) at day 10, corresponding at 159 μM and 227 μM adenosine. These results show that both liposomal formulations are good reservoirs for encapsulation and slow release of adenosine in concentrations sufficient to activate A2A receptor in vivo.

The efficacy of the newly developed formulations was further tested in the post-traumatic OA (PTOA) rat model. As described above, rats develop OA after mechanical rupture of the ACL. PTOA rats were randomized to experimental groups. Incapacitance pain tests were performed prior to beginning the experiment. Animals were divided into 10 groups, to receive RgnA09 or RgnA10 at 0 (empty liposome/vehicle), 0.3, 1, or 3 mg/ml of adenosine, saline, or formulation, as described previously in Corciulo et al. Animals received one injection every 10 days, 6 times. Knee swelling was measured before every injection as a measure of articular inflammation. Pain test was performed in rats at baseline (before first injection), at 30 days (mid-term of the treatment regimen), and right before sacrifice (7 days after the last injection). Post-sacrifice joints were analyzed using histology and uCT. Pain behavior was measured as weight bearing asymmetry between the ipsilateral and contralateral hind limbs by incapacitance meter (FIG. 9).

After the hyperalgesia test, animals were placed in rodent restrainers to stand on hind paws, with hind limbs resting on two weight-averaging platform pads. As the animal shifted their weight from each pad, the unit recorded the average weight in grams over 12 seconds for 3-4 consecutive measurements. The mean value for each animal was used for analysis. Motor ability was also measured using the rotarod test, which provides assessment of motor function with pressure and stress on the knee joint. Rats were placed onto an accelerating rotarod, and failure to stay atop the rod was measured and used for further analysis (data not shown). Based on the incapacitance test, there was a strong dose interaction between vehicle and 1 mg/ml for RgnA09, and between 0.3 mg and 3 mg with RgnA10. In addition, at 30 days (after 3 injections) we observed a steady trend of a dose response in the reduction of joint pain with both formulations, with all doses significantly different from vehicle for Rgn09, and 3 mg of Rgn10 different from Rgn01 and vehicle. The rotarod test also showed a dose response trend and a difference at 60 days with the highest dose of Rgn10 (3 mg/ml). In addition, we observed remarkable changes in joint inflammation with both formulations, with some doses showing significant differences to vehicle and saline after 6 injections. There was a steady decrease in joint inflammation over time with both formulations at 3 mg/ml (FIG. 15). Both Rgn09 and Rgn10 may be used at the highest dose of 3 mg/ml.

Example 6

This example provides a methods of using liposomes of the present disclosure.

Liposomal Adenosine preparation. Liposomal Adenosine (RgnA09) was prepared using our proprietary lipid composition and manufacturing processes. To study the effect of lipid concentration, particle size and freeze thaw cycles on the drug formulation, sub-batches of the liposomes were prepared by varying the lipid content (10-100 mg), extruding the liposomes using various sizers (100-100 nm) and conducted 4 freeze thaw cycles. The effect of these parameters were measured by analyzing preliminary attributes such as EE %, particle size and polydispersity index (PDI). Analytical methods for assessing EE % of adenosine in liposome formulations were developed, previously developed using reverse-phase high performance liquid chromatography (HPLC) with UV detection. Analytical methods for assessing lipid concentration in liposome formulations were previously developed using reverse-phase high performance liquid chromatography with evaporative light scattering detector (ELSD) detection.

Figure 17:
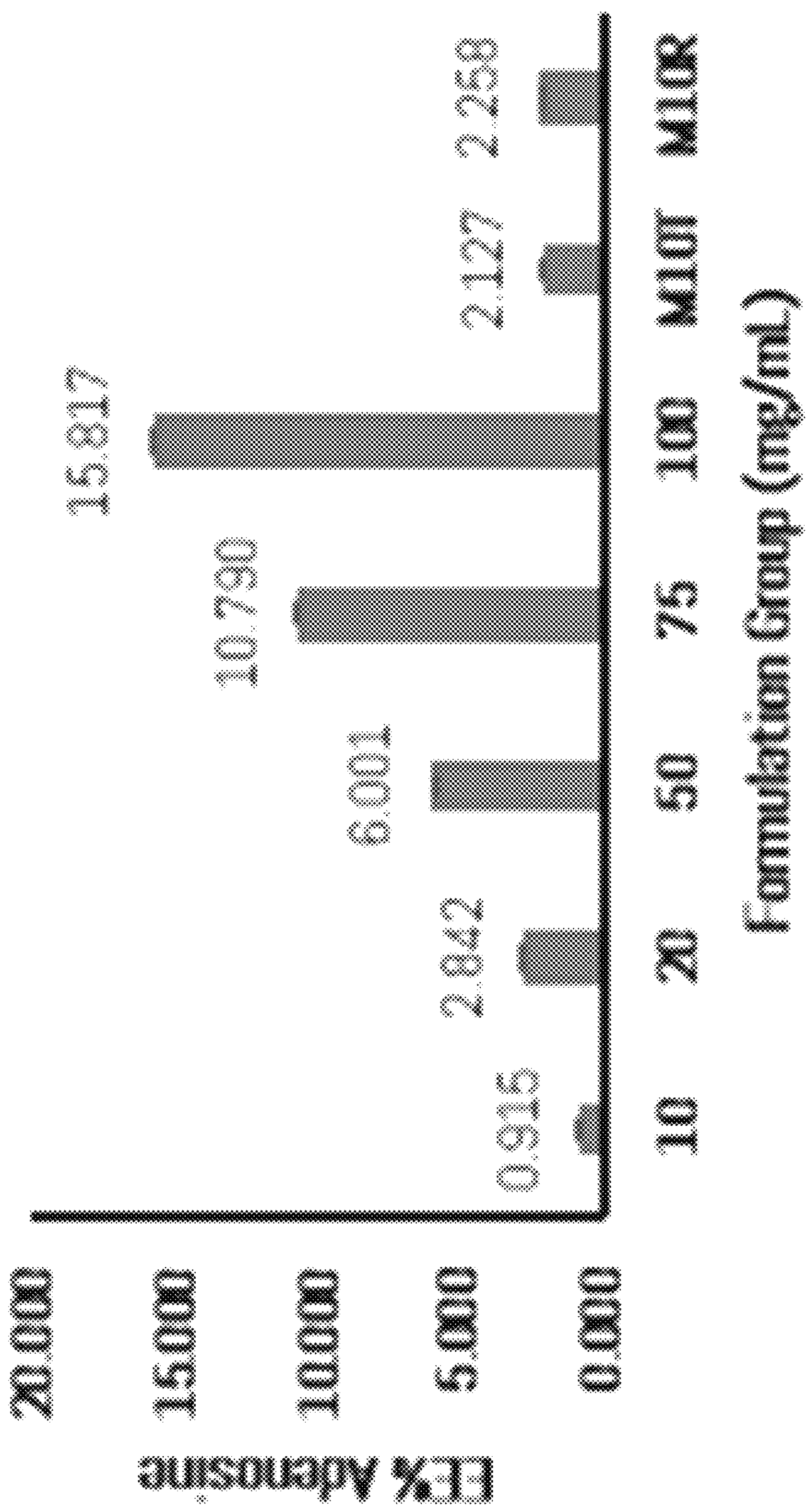
FIG. 17 shows a bar graph illustrating comparative analysis of adenosine EE % within SUV containing 10, 20, 50, 75, and 100 mg/mL lipid in sample preparations. These results are also compared to traditional 10 mg/mL MLV samples.

Adenosine encapsulation. Adenosine encapsulation was optimized with thin-film hydration and extrusion to investigate the relationship of adenosine encapsulation efficiency (EE %) and starting total lipid concentration, and to investigate the relationship of adenosine encapsulation efficiency (EE %) and starting total lipid concentration, and to investigate the relationship of adenosine EE % to final size of Ade-encapsulated SUV as determined by extrusion parameters. The increase in lipid concentrations to 100 mg/ml had a direct correlation to the EE % (FIG. 17).

The EE % of Ade-encapsulated liposomes was determined using the ratio of $C_{encap}$ and $C_{total}$ while ensuring proper consideration of dilution concentration factors of the liposomes within the processing method. To measure the total adenosine ($C_{total}$) the liposomes were diluted in 6% Triton X-100 and heated at 55° C. in water bath for 5 minutes to promote liposome disruption and release Ade from liposomes for $C_{total}$ analysis. To measure the encapsulated adenosine ($C_{encap}$), the liposomes were diluted spun down using a 15 mL Amicon centrifugal spin filter with 100 kDa molecular weight cutoff and processed for analysis with RP-HPLC/UV using a Agilent Poroshell 120 EC-$C_{18}$ Column.

Figure 18:
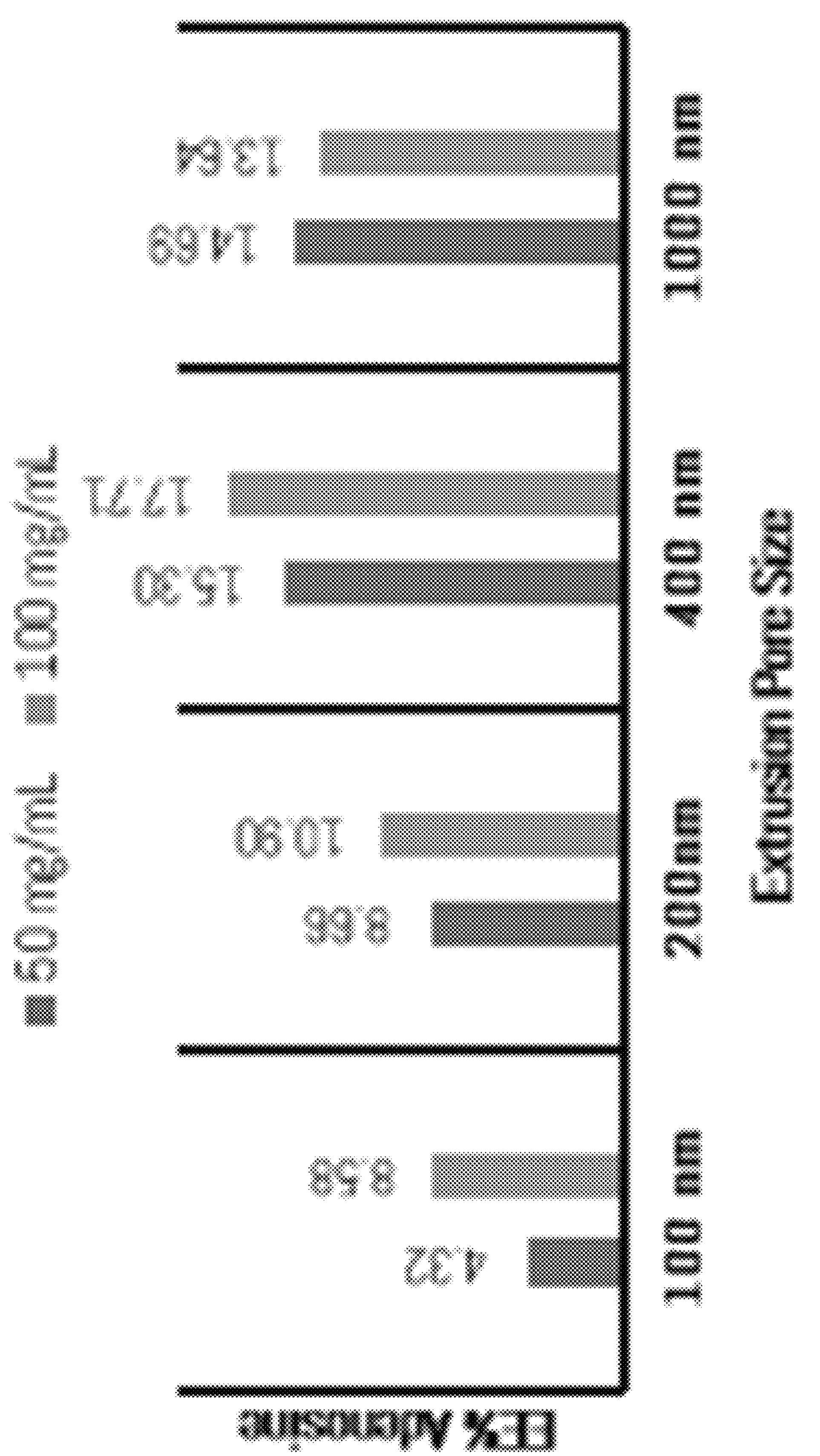
FIG. 18 shows a bar graph illustrating comparative analysis of Ade EE % as a function of nanoscale extrusion pore size for 50 and 100 mg/mL liposome preparations.
Figure 19:
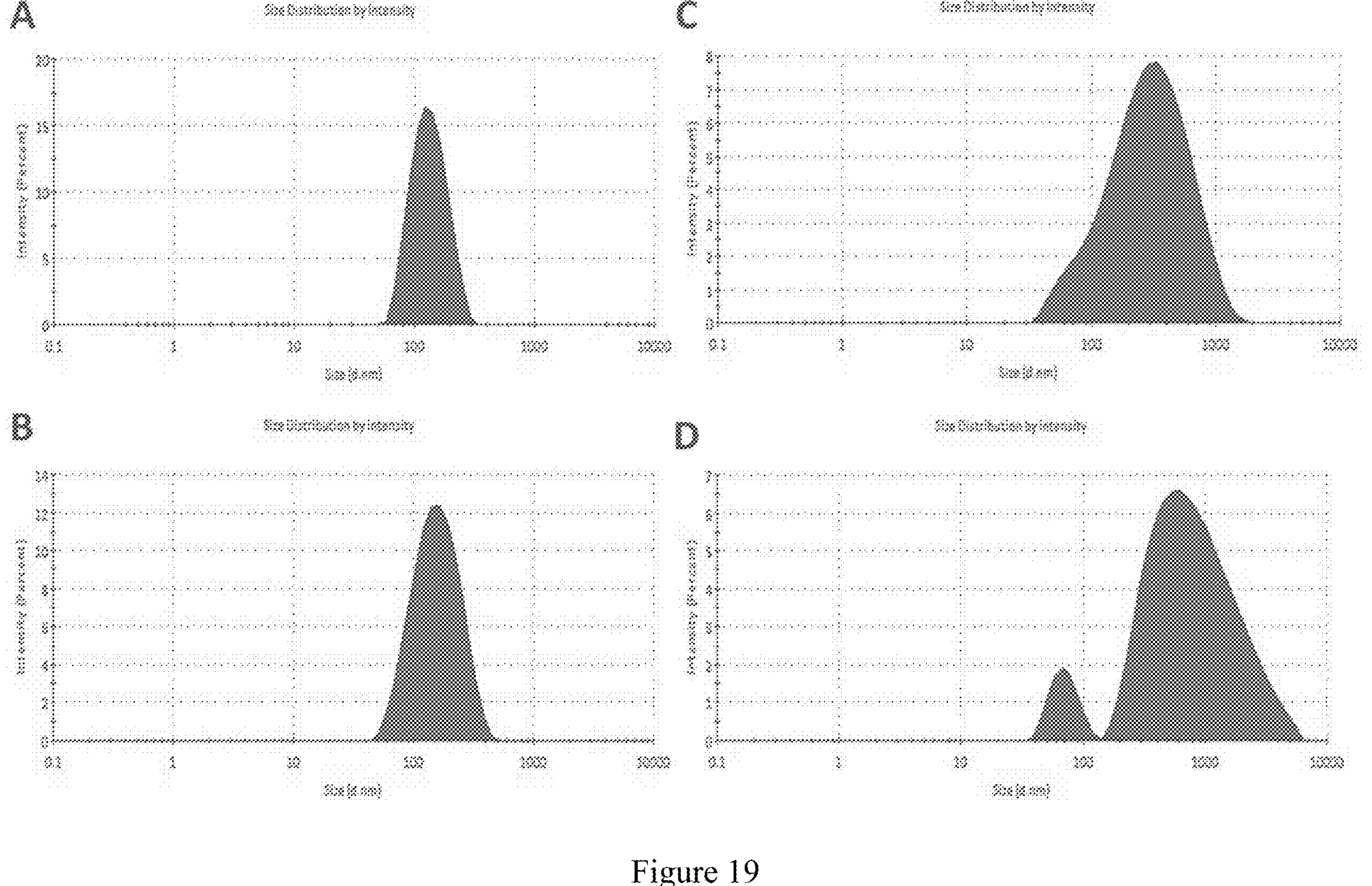
FIG. 19 shows size distribution by intensity graphs generated by DLS size and PDI data for 50 mg/mL liposomes samples (A—100 nm, B—200 nm, C—400 nm, D—1000 nm) and 100 mg/mL liposomes samples (E—100 nm, F—200 nm, G—400 nm, H—1000 nm).
Figure 19:
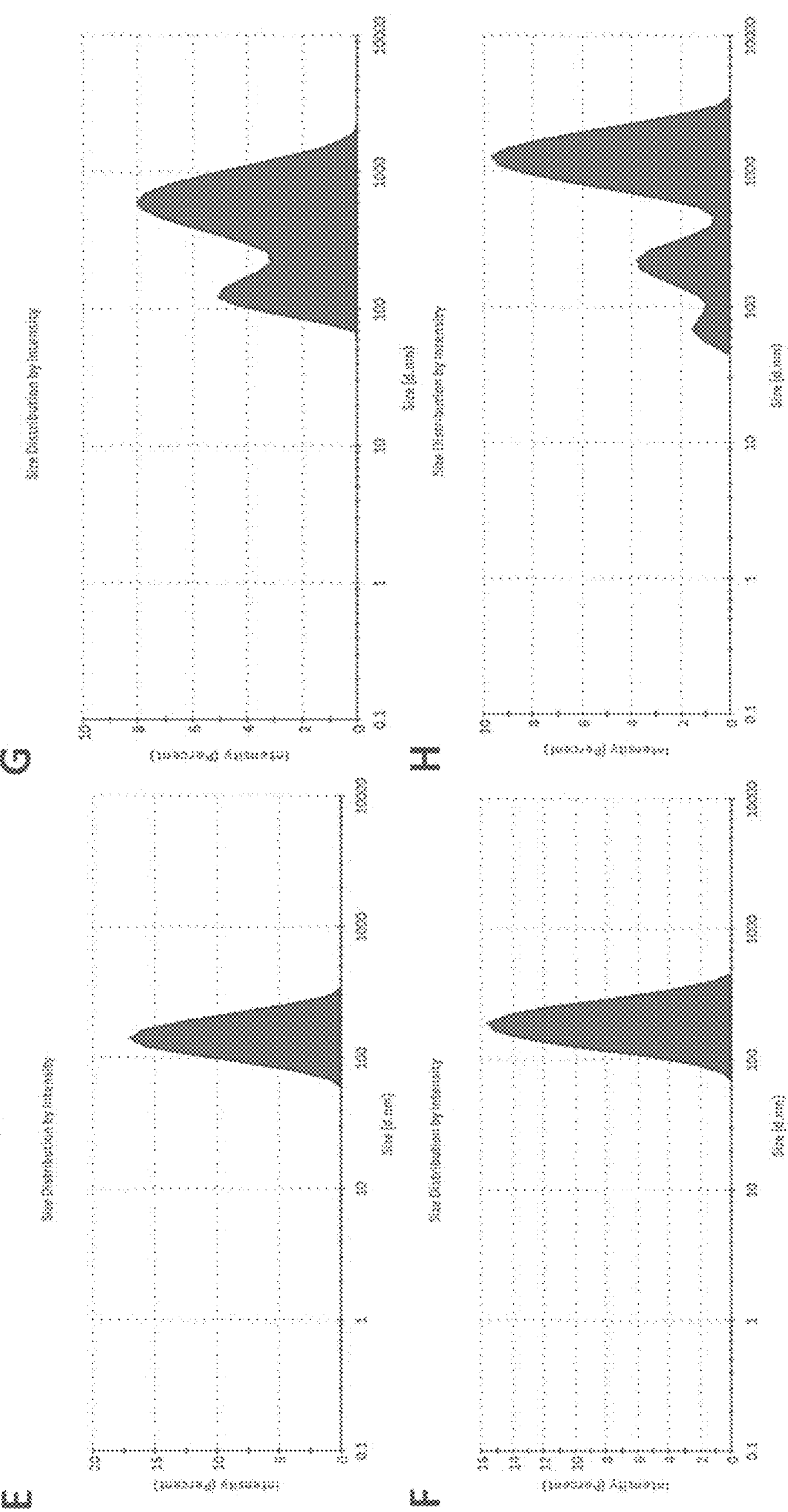
Figure 20:
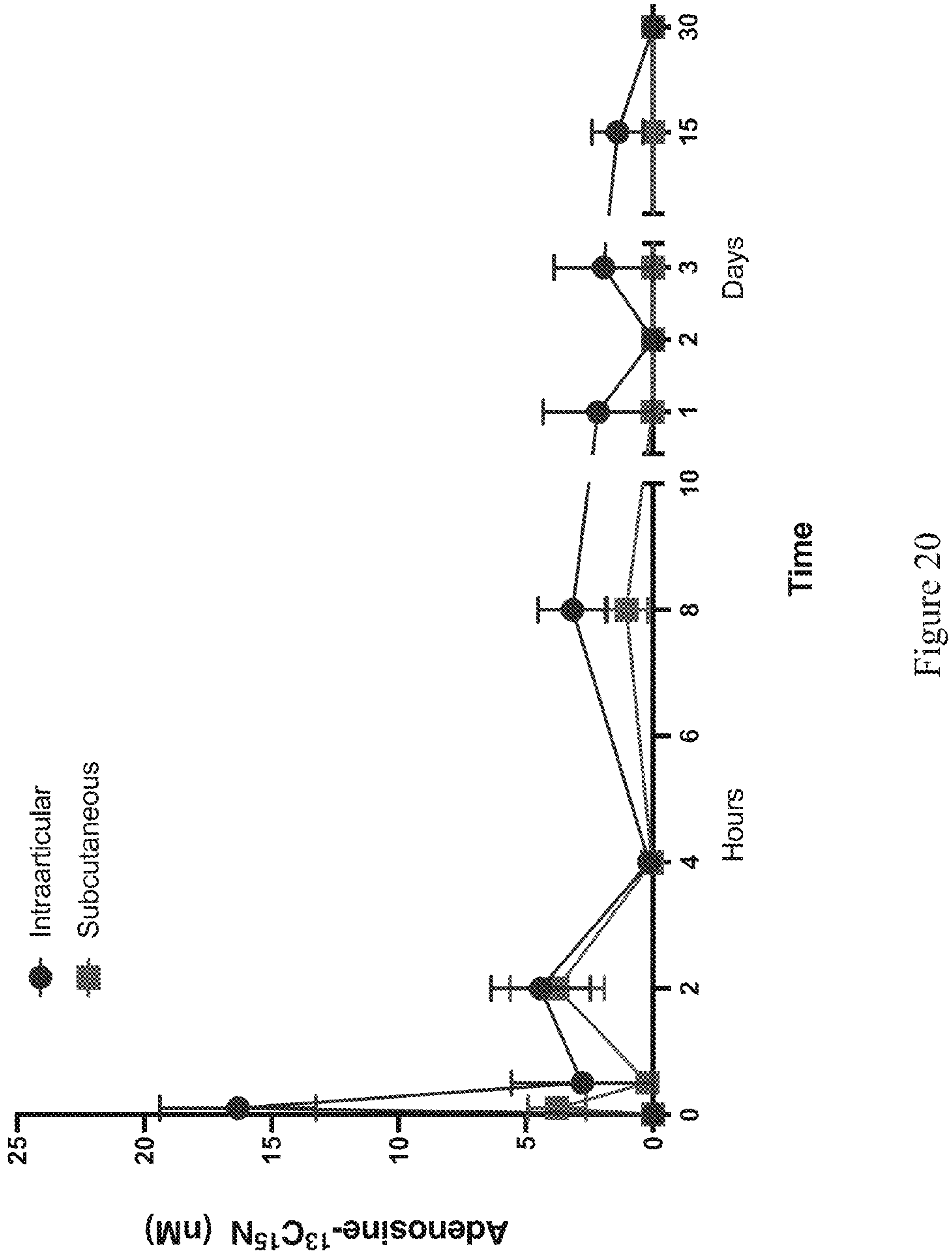
FIG. 20 shows pharmacokinetics of liposomal-adenosine-$^{13}C^{15}N$ RgnA09M.

A range of liposomal-adenosine (RgnA09) were prepared using step-down extrusion procedure followed by 4 freeze-and-thaw cycles. Comparative analysis of Ade EE % in initial study with varying nanoscale extrusion pore size revealed an impact on the EE %. (FIG. 18). The particle size polydispersity of Ade-encapsulated liposomes was measured in triplicate measurement runs to determine the mean Z-Ave (d.nm) and PDI of final Ade-encapsulated liposome product to confirm differences in average nanoscale size range of liposomes manufactured with varying extrusion pore size (FIG. 19).

Evaluate efficacy of liposomal formulation of adenosine for pain relief and maintenance of function and cartilage structure in dogs.

Ten male and eleven female purpose-bred hounds (20-32 kg) were housed at The University of Missouri Animal Resource Center. Arthroscopic medial meniscal release was performed on the right knee. Functional and diagnostic imaging evidence for OA was documented at two months after surgery (pre-Tx). At two months, dogs were sedated to allow the right knee to be injected with 3 mL of liposomal-adenosine RgnA09-MLV or RgnA09M (3 mg/ml; N=7), liposomal-adenosine RgnA09-200 nm or RgnA09N (3 mg/ml; N=7) or saline (0.9 mg/ml NaCl; N=7) for a total of 3 intra-articular injections, each done one month apart. All animals were humanely euthanized 6 months after initiation of treatment. Clinical lameness evaluation, function (VAS), clinical range of motion (C-ROM), effusion (VAS), pain (VAS) and force-mat gait analysis was performed once before surgical induction of OA, then again at two months, at mid-term of the treatment (4 months) and finally before euthanasia (6 months). Pain was assessed by direct observation of lameness, gait analysis using a force-mat apparatus that utilizes sensors to collect data on joints including the discrepancy between the pressure profile of each paw. The Glasgow University Veterinary School Questionnaire and canine brief pain inventory (CBPI) was used to score pain. Blood for plasma was collected before surgical induction of OA, then again at two months, at mid-term of the treatment (4 months) and finally before euthanasia (6 months). In addition, synovial fluid was collected after before surgical induction of OA, then at mid-term of the treatment (4 months) and euthanasia (6 months). Radiographic assessment of the knee joints were performed before surgical induction of OA, at mid-term of the treatment (4 months) and finally before euthanasia (6 months). MRIs were used to evaluate cartilage structure and integrity at two months after surgical induction of OA and finally before euthanasia (6 months). Gross evaluation, histology and histopathology were conducted to identify the effectiveness of the treatment. Immediately after sacrifice, the right and left hindlimbs were harvested. Photographs of the femoral groove and condyle and the tibial plateau before and after removal of the meniscus were taken for macroscopic evaluation of cartilage damage. For microscopic and histological evaluation were performed on fixed knee samples. Histology and immunohistochemistry allows us to evaluate changes in articular chondrocyte morphology, presence of fibrillation and cleft area on the cartilage surface, grade of proteoglycan and collagen loss, and release of metalloproteinases. Contralateral normal knees were used for controls for each outcome measure.

Knee pain, function and CROM were assessed subjectively by a board-certified veterinary orthopaedic surgeon using a 10 cm visual analogue scale (VAS) and a validated grading system, as previously described. Clinical lameness scores were determined for each dog based on visual examination of gait by the same board-certified veterinary orthopaedic surgeon using a 10 cm visual analogue scale (VAS) and a validated grading system. Radiographic scoring was modified from methods known in the art, to include effusion and sclerotic categories. Functional and diagnostic radiographic evidence for OA was documented at two months after surgery, before the treatment began. All dogs had significantly ($p<0.001$) more pain, more effusion, reduced function, and reduced comfortable range of motion (CROM) at two months after meniscal release, compared to baseline (pre-MR). At two months, osteoarthritic changes in the knee were observable with radiographs ($p<0.01$). Typically, untreated OA continue to progress until end stage OA, with progressive worsening in function, effusion, pain and CROM, and observable deterioration in the radiographs. Functional assessments and diagnostic imaging were performed at 2 months after the last injection (6 months after surgery).

Figure 22:
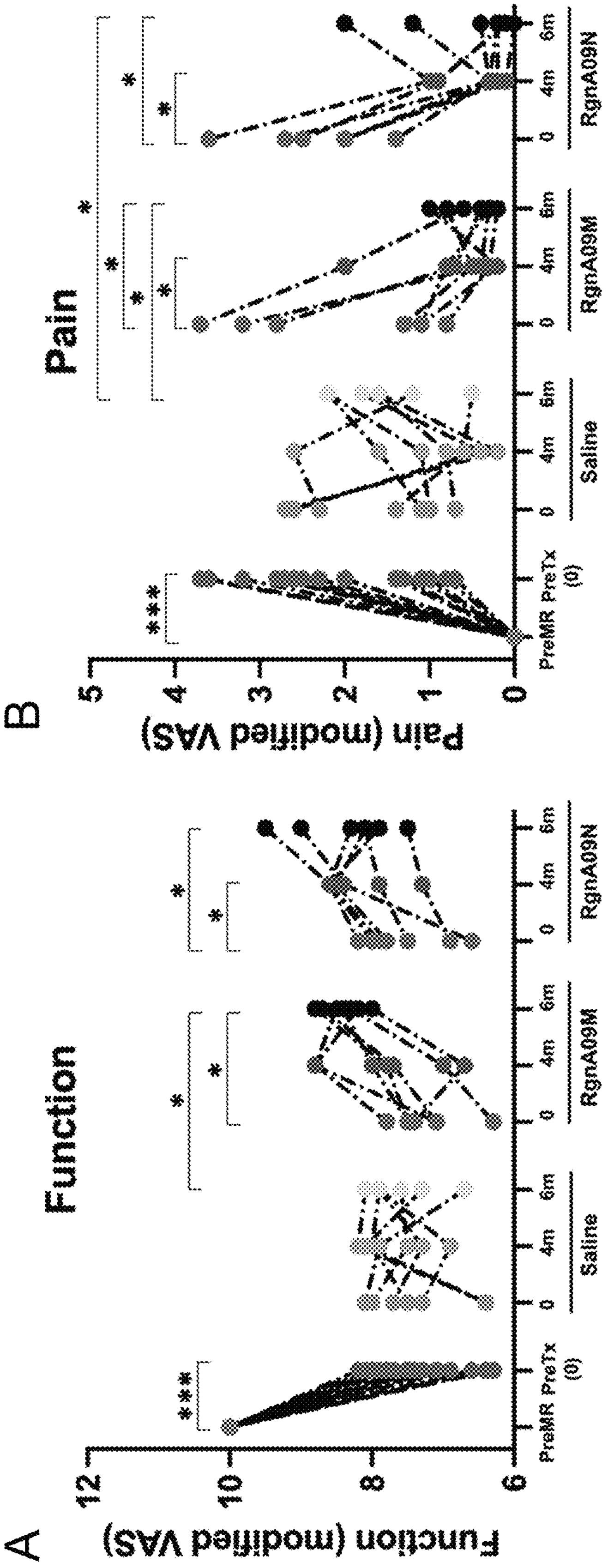
FIG. 22 shows evaluations of (A) Function, (B) Pain, (C) CROM, (D) Radiographic Score, (E) Effusion, and (F) MRI. The IA administration of RgnA09M, consistently showed a drastic progressive improvement over time in function, improved CROM to near-normal values and reduced pain up to 6 mo compared to pre-treatment. This further strongly correlated with significantly less radiographic severity in joint OA and less severity in the joint OA, compared to saline on MRI. Wilcoxon matched pair signed rank test was used for statistical analyses (*P<0.05, P<0.01, *P<0.001).
Figure 22:
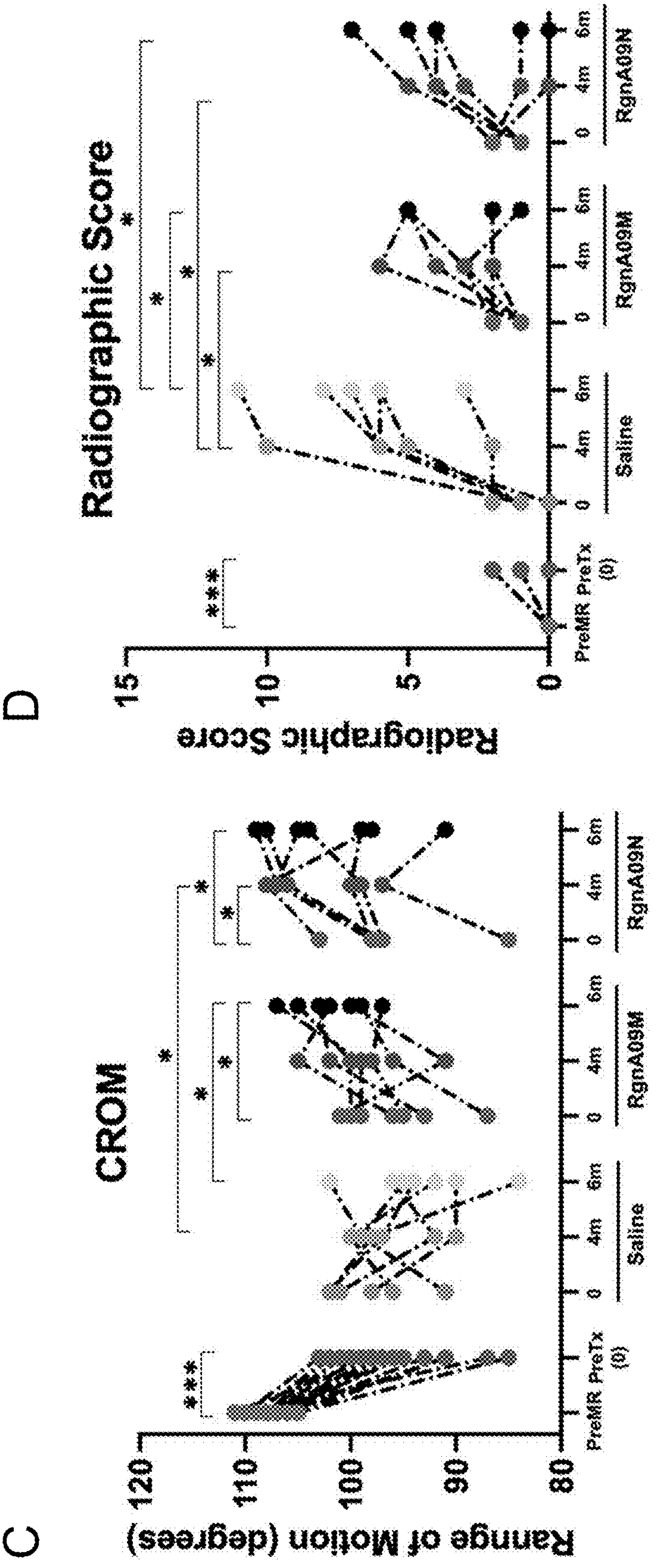
Figure 22:
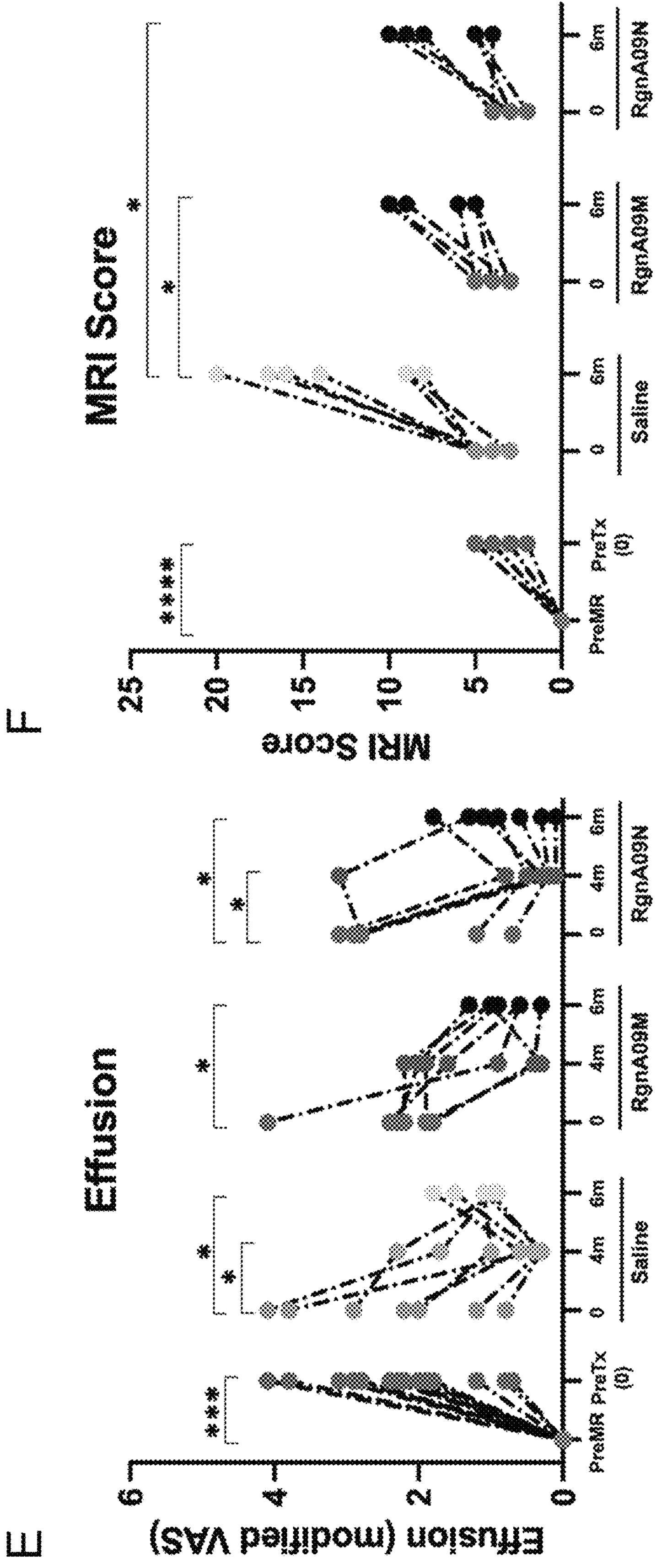
Figure 23:
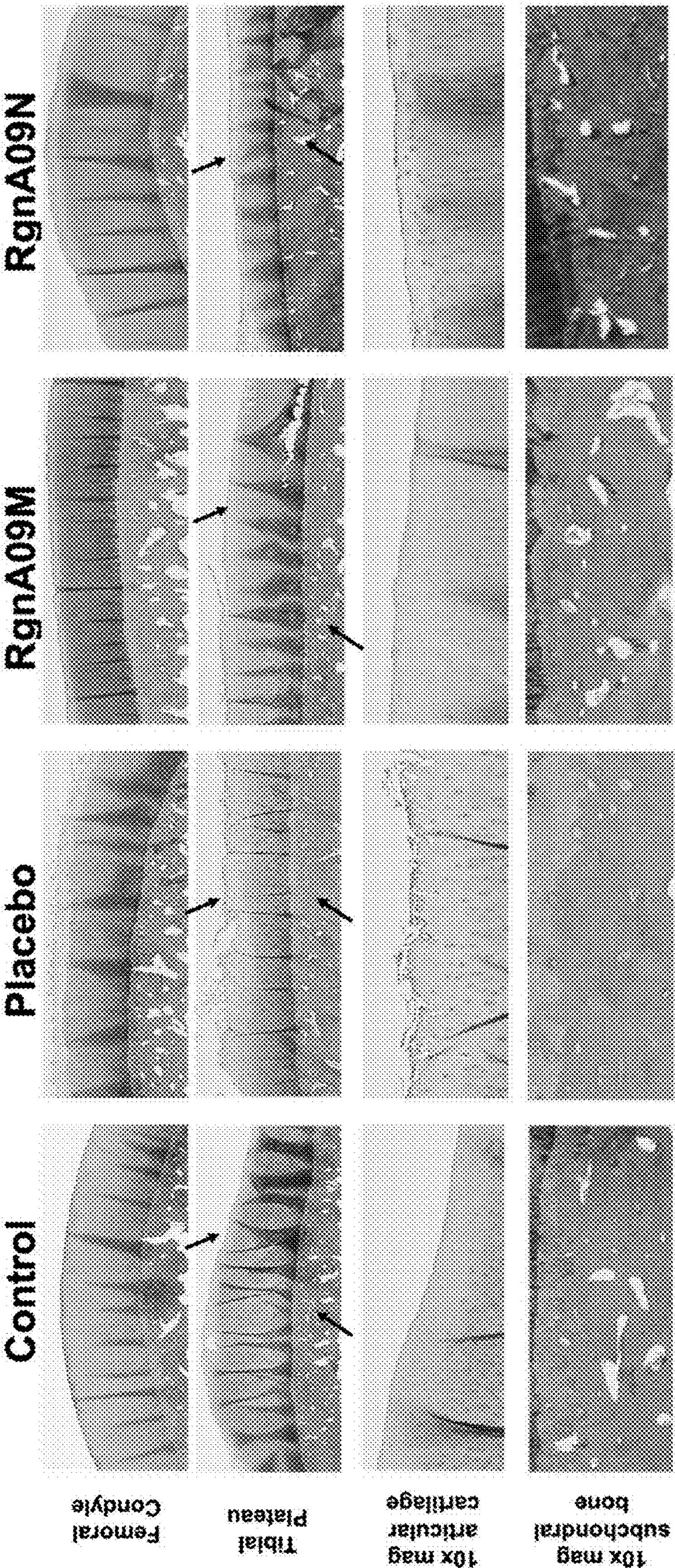
FIG. 23 shows hematoxylin and eosin staining of the knee joint cartilage tissues in different treatment groups. 10× magnification of the articular cartilage and subchondral bone area of the tibial plateau marked by arrows in the panel above.
Figure 24:
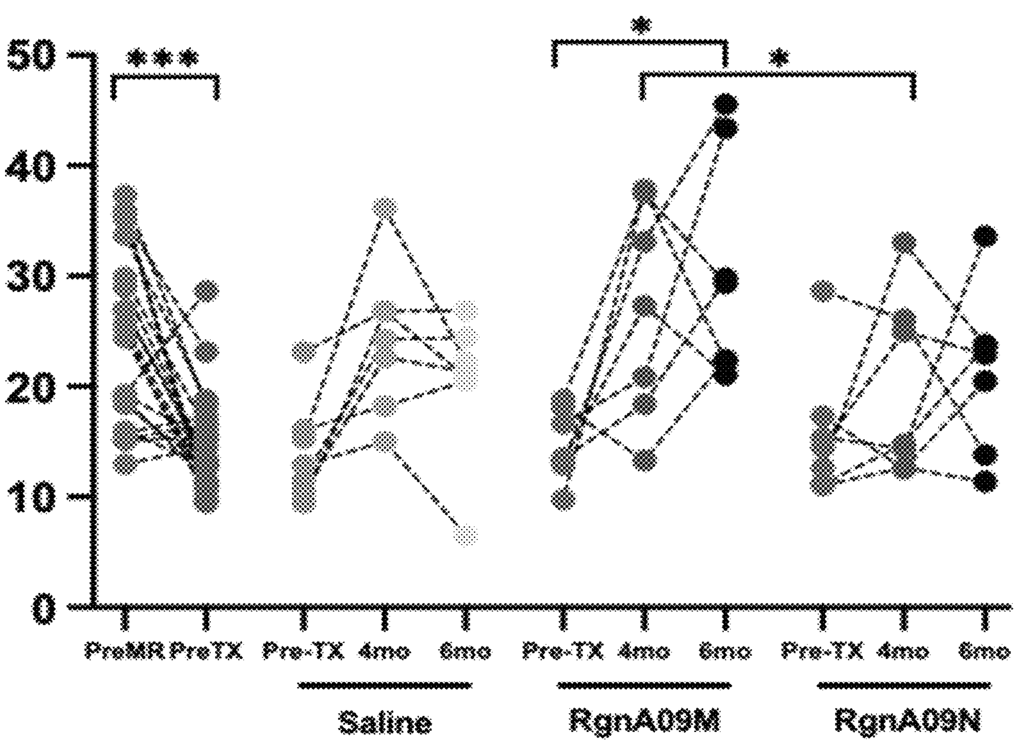
FIG. 24 shows ratio of COMP levels over CTX-II levels in the synovial fluid.

Improvement of function and CROM with RgnA09M: At 2 mo post-MR, there was an average 26.3% loss in function and an average 10% loss in comfortable range of motion (CROM) in all dogs. These losses persisted at 4 and 6 mo with no significant changes, with saline treatment. Treatment with RgnA09M resulted in 30.9% improvement in function at 4 mo, rising to 61.8% at 6 mo compared to pre-treatment ($p<0.05$). Treatment with RgnA09N resulted in 39.7% improvement in at 6 mo, compared to pre-treatment ($p<0.05$) (FIG. 22A). Saline-treated animals experienced an additional 13.0% loss of CROM by 6 mo, while treatment with RgnA09M improved CROM to near-normal values at 6 mo, showing a significant improvement over saline treatment (FIG. 22C). RgnA09N also showed improvement but without statistical significance.

Long-term pain relief: Joint pain in all dogs increased from 0 at baseline to a score of 2.0±0.9 at 2 mo post-MR, as assessed using a 10 cm visual analogue scale and a validated grading system. Saline treatment did not improve pain, while RgnA09M reduced pain by 65.0% at 4 mo and 74.3% at 6 mo ($p<0.05$). RgnA09N reduced pain by 80.9% at 4 mo post-treatment, and by 74.7% at 6 mo ($p<0.05$). Compared to saline, both formulations reduced pain at 6 mo post-treatment ($p<0.05$) (RgnA09M: 67.9%; RgnA09N: 63.2%) (FIG. 22B).

Effusion Improvements: Progressive increase was observed in joint effusion with a score of 2.3±0.9 at 2 mo post-MR. Following saline treatment, significant improvements in the joint effusion were noted at 4 mo (0.94±0.78) and 6 mo (1.20±0.33) post-MR. Rgn09M improved joint effusion by 44.0% (non-significant) at 4 mo post-MR in comparison to pre-treatment and maintained improvement by 65.7% (6 mo post-MR vs. pre-Tx, $p<0.05$). With RgnA09N, there was a significant improvement in effusion, 81.8% over pre-treatment at 4 mo post-MR ($p<0.05$) and by 62.6% at 6 mo post-MR ($p<0.05$) (FIG. 22E). No observable improvements among Saline, RgnA09M, and RgnA09N treatments were found.

Radiographic improvements in the knee joint with RgnA09M treatment: Progressive deterioration in the joint occurs after MR surgery. Following saline treatment, radiographic changes worsened in severity (score 5.7±2.4 at 4 mo and 6.7±2.4 at 6 mo). In RgnA09M and RgnA09N treated joints, there was 33.3% and 45.8% significantly less severity, respectively, in joint OA at 4 mo after treatment, ($p<0.05$). At 6 mo after treatment, both treatments resulted in 42.6% less severity in joint OA compared to saline ($p<0.05$) (FIG. 22D). Progressive changes in cartilage structure and surrounding soft tissue is better visualized on an MRI (score 3.7±1.0 at 2 mo post-MR, $p<0.0001$). Saline treatment further worsened the joint (score 4.6±0.8). In the RgnA09M and RgnA09N treated joints, at 6 mo after treatment, there was 55.3% and 42.8% significantly less severity in the joint OA, respectively, compared to saline ($p<0.05$) (FIG. 22F).

With histology and histopathology, mild to moderate OA of articular cartilage was observed in all dogs 2-mo post-MR, most severely in the medial tibial plateau. Saline resulted in the most severe changes, marked by fibrillation of articular cartilage (arrow), synovitis and subchondral bone plate thickening (arrow). Joints treated with RgnA09M or RgnA09N were protected from these changes and scored lower on global total histology scores, at 6 mo post-treatment, with evidence of cartilage regeneration (arrow) and corresponding recovery of the subchondral bone (arrow) (FIG. 12).

RgnA09M treatment also resulted in a significant decrease in crosslinked C-telopeptides of type II collagen (CTX-II) levels at 4 mo, and significant increase in cartilage oligomeric matrix protein (COMP) levels at 6 mo, in comparison to placebo or RgnA09N the two biomarkers which can potentially predict the destruction of articular cartilage of early OA. He ratio of COMP over CTX-II significantly increased with RgnA09M treatment, representing an increase in the anabolic effects while decreasing the catabolic changes in the cartilage (FIG. 29).

The lamellarity and size of the liposome have an impact on the % EE, and stability and hence the release kinetics and dosage of the adenosine. It was previously demonstrated in literature that at 4 months post-MR the canine joint shows severe signs of OA with severe loss in function, increased effusion, increased pain and severe loss in CROM, with observable deterioration in radiographs. Untreated, OA progressively worsens as time progresses in this model of PTOA. We have demonstrated that we can significantly slow the progression of OA with intra-articular treatments of RgnA09 until 6 mo after treatment, significantly reduce the pain and significantly improve joint function and ROM. We have further demonstrated that lamellarity and size of the liposome have a measurable impact on the extent of efficacy. The current findings, particularly CROM, pain, effusion and radiographic score are of significance as they directly translate to measurable outcomes in a human clinical setting.

Example 7

This example provides a methods of using liposomes of the present disclosure and it also shows a pharmacokinetic study of adenosine in rat plasma.

In-life procedure and sample collection. Crl:CD (SD) rats (N=5) received three intra-articular injections of liposomal-adenosine-$^{13}C^{15}N$ RgnA09M (3 mg/ml), one injection per day. All three injections were administered into the left knee joint. Another experimental group of rats (N=5) received three subcutaneous injections administered directly adjacent to the left knee joint using the same dosing schedule to evaluate the adenosine-$^{13}C^{15}N$ content in the blood stream to model potential errors in injection of liposomal-adenosine-$^{13}C^{15}N$. Blood was collected from the tail vein using a single 2 mm tail tip amputation before dosing began (baseline), immediately after 3rd injection (0 hr) and after 0.5, 2, 4, 8, 24, 48, 72 hours, 15 days and 30 days in vials containing 25 mM EDTA, 1 μM deoxycoformycin, and 10 μM dipyridamole. The blood was spun down at 3,000 g for 10 min at 4° C. and the plasma separated. Plasma vials were frozen immediately and store at −80° C. until ready for analysis. In addition, some animals were sacrificed after 48 hours, 72 hours, 15 days, and 30 days, and their synovial fluid and blood were collected. Synovial fluid was processed similar to the blood. All synovial fluid and plasma were analyzed for native adenosine, native inosine, adenosine-$^{13}C^{15}N$, inosine-$^{13}C^{15}N$ using LC-MS/MS.

Analysis with LCMS/MC was performed. Extraction of Adenosine from Plasma: Prior to extraction, samples were moved from −80° C. storage to wet ice and thawed. Extraction buffer, consisting of 82% methanol (Fisher Scientific), 1% formic acid (Millipore Sigma), 5 nM $^{13}C$-5 adenosine (Cambridge Isotope Laboratories, Inc.), 50 nM $^{15}N$-4 inosine (Cambridge Isotope Laboratories, Inc.), and 512 nM metabolomics amino acid mix standard (Cambridge Isotope Laboratories, Inc.), was prepared and placed on dry ice. A standard curve was generated in null rat plasma using uniformly labeled $^{13}C^{15}N$-Adenosine, the drug formulation (Millipore Sigma) in marked 2 mL glass volumetric flasks. First a 10 μM $^{13}C^{15}N$-Adenosine solution was prepared in water. Then a serial dilution was made with the following nine curve points: 1 μM, 300 nM, 100 nM, 30 nM, 10 nM, 3 nM, 1 nM, 300 μM, 100 μM. Samples and curve points were extracted by mixing 25 μL of sample with 975 μL of extraction buffer in 2.0 mL screw cap vials containing ~100 μL of 0.5 mm Zircon disruption beads (Research Products International, Mount Prospect, IL). Each sample was homogenized for 10 cycles on a bead blaster homogenizer (Benchmark Scientific, Edison, NJ). Cycling consisted of a 30 sec homogenization time at 6 m/s followed by a 30 sec pause. Samples were subsequently spun at 21,000 g for 3 min at 4° C. A fixed volume of each sample (450 μL) was transferred to a 1.5 mL tube and dried down by speedvac (Thermo Fisher, Waltham, MA). Samples were reconstituted in 50 μL of Optima LC/MS grade water (Fisher Scientific, Waltham, MA). Samples were sonicated for 2 min, then centrifuged at 21,000×g for 3 min at 4° C. 20 μL were transferred to LC vials containing glass inserts for analysis. The remaining sample was placed in −80° C. for long term storage.

LC-MS/MS targeted quantification of Adenosine: Samples were then subjected to an LCMS analysis to quantify Adenosine and Inosine. The LCMS parameters were adapted from a previously described method. The LC column was a Waters™ BEH-Phenyl (2.1×150 mm, 1.7 μm) coupled to a Dionex Ultimate 3000™ system and the column oven temperature was set to 25° C. for the gradient elution. A flow rate of 200 μL/min was used with the following buffers; A) 0.1% formic acid in water, and B) 0.1% formic acid in acetonitrile. The gradient profile was as follows; 0-35% B (0-10 min), 35-75% B (10-15 min), 75-99% B (15-15.25 min), 99-99% B (15.25-16.5 min), 99-0% B (16.5-16.75 min), 0-0% B (16.75-20 min). Injection volume was set to 5 μL for all analyses (20 min total run time per injection).

MS analyses were carried out by coupling the LC system to a Thermo Q Exactive HF™ mass spectrometer operating in heated electrospray ionization mode (HESI). Spray voltage for positive mode was 3.5 kV and capillary temperature was set to 320° C. with a sheath gas rate of 35, aux gas of 10, and max spray current of 100 μA. Method duration was 20 min with multiplexed PRM to confirm compound ID for m/z 268.1040 (Unlabeled Adenosine), 273.1208 ($^{13}C$ Adenosine), and 283.1228 ($^{13}C1,^{15}N$ Adenosine) in positive mode. MS settings were; microscans: 1, AGC target: 1e5, Maximum IT: 50 ms, loop count: 1, MSX count: 3, isolation window: 0.4 m/z, isolation offset: 0.0 m/z, fixed first mass: 50.0 m/z, and (N) CE/stepped nce: 10, 35, 80.

A SIM scan was used for quantification of Adenosine and Inosine. MS settings were; microscans: 1, AGC target: 3e6, Maximum IT: 200 ms, scan range: 200 to 300 m/z. All data were acquired in profile mode.

In the current study, we used a heavy labeled adenosine to differentiate the adenosine derived from the drug from the native adenosine. The average native adenosine in a normoxic rat plasma has been previously reported to be 79.2±12.7 nM, although this can be extremely variable based on several physiological and environmental factors. After three (3) injections of $^{13}C^{15}N$ RgnA09M, there was a sharp increase at 30 mins, in the circulating plasma adenosine-$^{13}C^{15}N$ to 16.32±6.1 nM with the intra-articular injection in comparison to 3.80±2.7 nM with the sub-cutaneous injections. The circulating plasma adenosine-$^{13}C^{15}N$ levels decreased rapidly reduced and were maintained between 4.4 nM to 1.4 nM, in the intra-articular injection group, up to 15 days after the injection after which no adenosine-$^{13}C^{15}N$ was detected in the blood plasma. In contrast, the circulating plasma adenosine-$^{13}C^{15}N$ levels decreased rapidly reduced and were maintained between 3.7 nM to 40 μM, in the sub-cutaneous injection group, up to 24 hours after the injection, after which no adenosine-$^{13}C^{15}N$ was detected in the blood plasma. This demonstrates that there is sustained release of the Adenosine from the liposomes in the joint for up to 15 days. In addition, with the subsequent injections, the increase in the systemic levels is nominal and any misuse (subcutaneous) injection will not result in systemic exposure or drug accumulation in the circulating blood. No circulating Inosine-$^{13}C^{15}N$ was observed in the circulating plasma in either groups throughout the study period.

Figure 21:
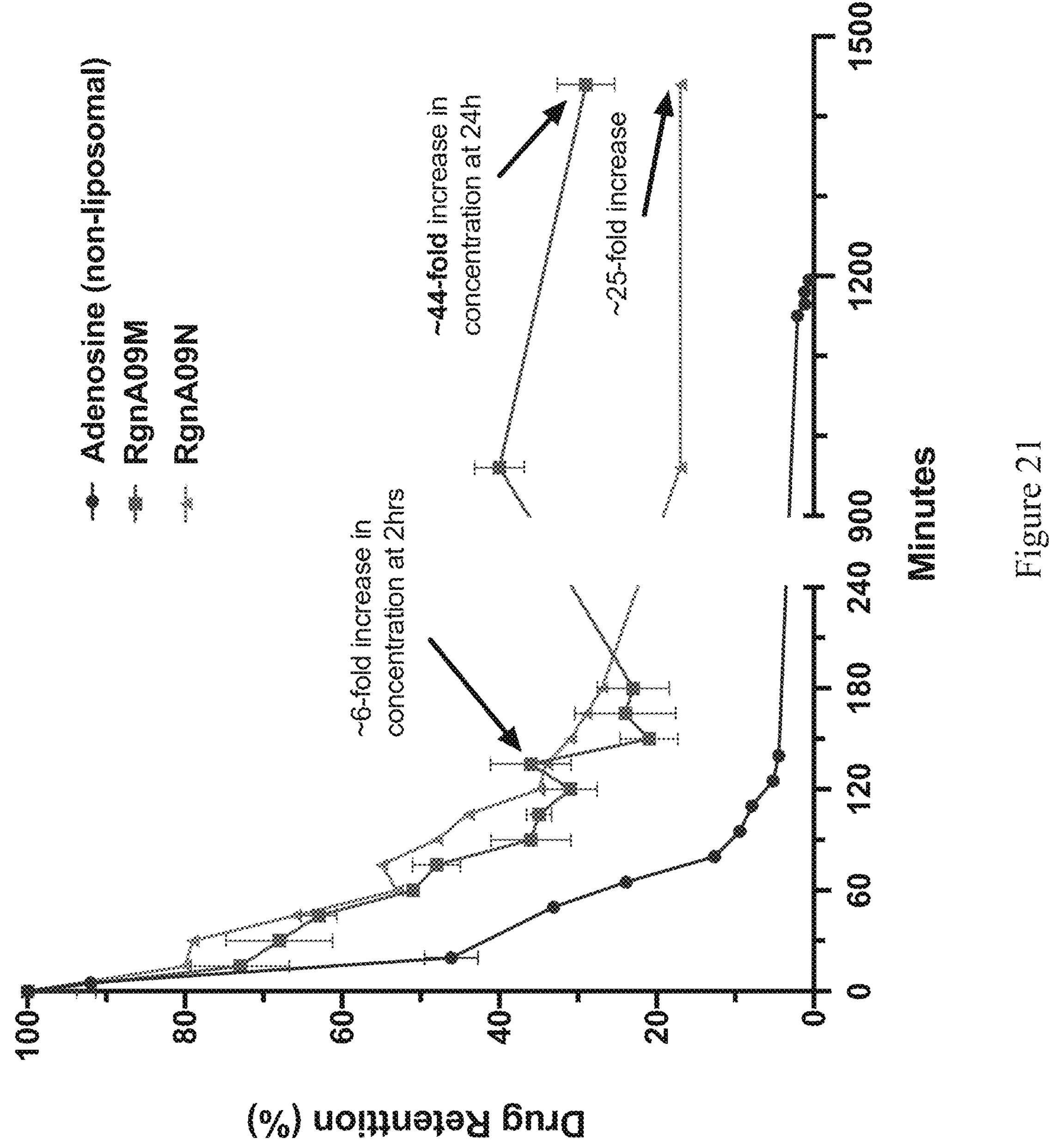
FIG. 21 shows in vitro dissolution of adenosine from liposomal-adenosine formulations (RgnA09M and RgnA09N) over 24 hrs.

In vitro Dissolution of RgnA09M and RgnA09N. RgnA09M and RgnA09N, which comprise identical lipid composition but vary in particle size and liposome lamellarity, offering distinct biological response due to release kinetics and longevity. RgnA09M is multilamellar and is larger, whereas RgnA09N is about 200 nm in diameter. In an in vitro passive dissolution assay with the use of 300 kD dialysis cassettes, we observed a release of adenosine over time. Both liposomal adenosine (RgnA09M and RgnA09N) formulations showed a longer sustained release while maintaining higher concentrations, than non-liposomal adenosine as expected. (FIG. 21). At 2-hours, they both presented a 6-fold increase in the concentration in comparison to non-liposomal adenosine. However, at 24-hours RgnA09M exhibited almost 2× the concentration of RgnA09N, with a 44-fold and 25-fold increase over non-liposomal adenosine respectively.

Although the present disclosure has been described with respect to one or more particular examples, it will be understood that other examples of the present disclosure may be made without departing from the scope of the present disclosure.

The invention claimed is:

1. An injectable formulation suitable for intra-articular injection comprising saline and liposomes comprising one or more lamellae, wherein the liposome lamellae consist of 70 to 99.9% by mass sphingomyelin, a sterol, 1,2-dimyristoyl-sn-glycero-3-phosphorylglycerol (DMPG), and optionally 1,2-dimyristoyl-sn-glycero-3-phosphocholine (DMPC), and (a) the liposomes have a diameter of 50 nm to 150 μm and (b) the liposomes encapsulate adenosine in the aqueous compartment of the liposome; and the total concentration of adenosine of the formulation is 1 to 3 mg/mL.

2. The injectable formulation according to claim 1, wherein the liposomes have a diameter of about 1 to 100 μm.

3. The injectable formulation according to claim 1, wherein the adenosine or a portion thereof is released for up to two weeks.

4. The injectable formulation according to claim 1, further comprising an excipient.

5. The injectable formulation according to claim 1, wherein DMPC is present and the ratio of DMPC and DMPG is 7:3.

6. The injectable formulation according to claim 1, wherein the total lipid concentration is 7 to 200 mg/mL.

7. The injectable formulation according to claim 1, wherein one or more of the liposomes have a diameter of 50 nm to 250 nm.

8. The injectable formulation according to claim 7, wherein the liposomes are unilamellar.

9. The injectable formulation according to claim 1, wherein the liposomes have been prepared via extrusion.

10. The injectable formulation of claim 1, wherein the sterol is cholesterol.

11. The injectable formulation of claim 1, wherein DMPC is present and the ratio of DMPC to DMPG is 6:4 to 8:2.

12. A method of i) inducing cartilage regeneration and/or ii) alleviating joint pain and/or inflammation and/or iii) slowing and/or arresting and/or reversing progressive structural tissue damage comprising administering to an individual a therapeutically effective amount of an injectable formulation according to claim 1, wherein i) cartilage regeneration is induced and/or ii) joint pain and/or inflammation is alleviated or partially alleviated and/or iii) progressive structural tissue damage is slowed or partially slowed and/or arrested or partially arrested and/or is reversed or partially reversed.

13. The method according to claim 12, wherein the injectable formulation is administered via intra-articular injection to a joint of the individual and/or is administered in one or more injections.

14. The method according to claim 12, wherein the individual has osteoarthritis, rheumatoid arthritis, acute gouty arthritis, and/or synovitis.

* * * * *